US009174390B2

(12) United States Patent
Lechmann et al.

(10) Patent No.: US 9,174,390 B2

(45) Date of Patent: Nov. 3, 2015

(54) INTEGRATED MULTI-MATERIAL IMPLANTS AND METHODS OF MANUFACTURE

(75) Inventors: Beat Lechmann, Langendorf (CH); Dieter Schmidli, Langendorf (CH); Robert Frigg, Langendorf (CH); Reto Nardini, Oberdorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 322 days.

(21) Appl. No.: 12/979,643

(22) Filed: Dec. 28, 2010

(65) Prior Publication Data

US 2011/0190904 A1 Aug. 4, 2011

Related U.S. Application Data

(60) Provisional application No. 61/291,126, filed on Dec. 30, 2009.

(51) Int. Cl.

| | |
|---|---|
| ***A61F 2/28*** | (2006.01) |
| ***A61B 17/56*** | (2006.01) |
| ***A61B 17/58*** | (2006.01) |
| ***A61B 17/80*** | (2006.01) |

(Continued)

(52) U.S. Cl.

CPC ......... *B29C 67/0077* (2013.01); *A61B 17/7208* (2013.01); *A61B 17/8085* (2013.01); *A61F 2/28* (2013.01); *A61F 2/3094* (2013.01); *A61F 2/442* (2013.01); *A61B 2017/00526* (2013.01); *A61F 2002/30014* (2013.01); *A61F 2002/30075* (2013.01); *A61F 2002/30563* (2013.01); *A61F 2002/30841* (2013.01); *A61F 2002/30971* (2013.01); *A61F 2002/30985* (2013.01); *A61F 2002/444* (2013.01); *B29L 2031/7532* (2013.01)

(58) Field of Classification Search

CPC ........................................................ A61F 2/28

USPC ........ 623/23.61–23.62, 23.51–23.58; 606/61, 606/69, 72, 246, 280–284, 298, 70, 71

See application file for complete search history.

(56) References Cited

U.S. PATENT DOCUMENTS 5,474,553 A * 12/1995 Baumgart ....................... 606/71
5,639,402 A 6/1997 Barlow et al.

(Continued)

FOREIGN PATENT DOCUMENTS

CN 101152103 4/2008
CN 101208051 6/2008

(Continued)

OTHER PUBLICATIONS

Chen et al., "Self Assembled Core-Shell Polymer Dielectric Prepaid by Solution Casting Process", Integrated Ferroelectrics, Jan. 1, 2009, 113(1), 1-8.

(Continued)

*Primary Examiner* — Yashita Sharma

(74) *Attorney, Agent, or Firm* — Baker & Hostetler LLP

(57) ABSTRACT

Provided are methods and systems for fabricating multimaterial bodies in a layer-wise fashion, which bodies may be used bone-stabilizing implants. The multimaterial bodies include rigid and flexible portions that are integrally formed with one another. The multimaterial bodies may be softened or stiffened in specific areas to match the biological or anatomical features of a bone.

29 Claims, 12 Drawing Sheets

(51) Int. Cl.

| | |
|---|---|
| ***B29C 67/00*** | (2006.01) |
| ***A61B 17/72*** | (2006.01) |
| ***A61F 2/30*** | (2006.01) |
| ***A61F 2/44*** | (2006.01) |
| *A61B 17/00* | (2006.01) |
| *B29L 31/00* | (2006.01) |

(56) References Cited

U.S. PATENT DOCUMENTS

| | | | | |
|---|---|---|---|---|
| 5,876,550 | A | 3/1999 | Feygin et al. | |
| 6,454,811 | B1 | 9/2002 | Sherwood et al. | |
| 7,641,676 | B2 | 1/2010 | Mathieu et al. | |
| 2004/0111089 | A1 | 6/2004 | Stevens et al. | |
| 2007/0093834 | A1 | 4/2007 | Stevens et al. | |
| 2007/0161997 | A1 | 7/2007 | Thramann et al. | |
| 2007/0191848 | A1 | 8/2007 | Wack et al. | |
| 2007/0239158 | A1 | 10/2007 | Trieu et al. | |
| 2008/0077141 | A1 | 3/2008 | Bray | |
| 2008/0208260 | A1 | 8/2008 | Truckai et al. | |
| 2012/0191139 | A1 * | 7/2012 | Stevens et al. | 606/281 |

FOREIGN PATENT DOCUMENTS

| | | |
|---|---|---|
| CN | 101394803 | 3/2009 |
| CN | 201227317 | 4/2009 |
| CN | 101448465 | 6/2009 |
| EP | 1911419 A2 | 4/2008 |
| WO | WO 2010/111350 | 9/2010 |

OTHER PUBLICATIONS

Hedges, “Laser Engineered net Shaping Technology and Applications”, info@neotechservices.com, Dec. 2009, 70 pages.

Sankare et al., “Fabrication Rapide Et Micro-Rechargement-Performances-Applications”, IrepaLaser , May 18, 2006.

* cited by examiner

INTEGRATED MULTI-MATERIAL IMPLANTS AND METHODS OF MANUFACTURE

CROSS-REFERENCE TO RELATED APPLICATIONS

The present application claims priority to U.S. Application No. 61/291,126, "Integrated Multi-Material Implant and Method of Manufacture," filed on Dec. 30, 2009, the entirety of which is incorporated by reference herein for all purposes.

TECHNICAL FIELD

The present disclosure relates to multi-material implants, and further relates to methods pertaining to additive manufacturing of multi-material implants.

BACKGROUND

Traditional bone joining implants, plates and related components for bone fixation are typically designed and manufactured from metals, polymers, allogenic, allograft or other materials that are integrally formed from a single piece of stock material. The size and shape of the bone joining implants are typically designed based on biomechanical characteristics of the bone that is being repaired by sizing the bone joining implant and fastening the bone joining implant to the bone with an appropriately sized device.

Some bone joining implants are designed with multiple components such as plates with screws or intramedullary nails with locking screws or other locking mechanisms. The bone joining implants may include multiple components in order to allow alignment of fracture fragments and/or alignment of adjacent bones. However, major components of the bone joining implants, such as a plate, nails or screws are designed and manufactured from a single piece of stock material, which allows limited control of mechanical properties of the subsequent bone joining implant and related components. It is thus desirable to construct bone joining implants and components that have material properties as close as possible to the biomechanical properties of the bone that is being repaired.

Wolff's law states that bone in a healthy person or animal adapts to loads that it is placed under. Accordingly, bone is grown in an area of high load and is resorbed or remodeled in areas of low load. When repairing fractures or joining bones, a bone joining implant that is too stiff creates a risk of bone resorption as excessive load is transferred to the bone joining implant and away from the bone. Bone joining implants that have low stiffness may result in an inability of the fracture to heal due to excessive movement at the fracture or implant breakage.

Important biomechanical aspects for internal fixation with bone joining implants include solid primary fixation to boney structure and sophisticated biomechanical behavior for fracture healing. For example, it may be desirable for the bone joining implant to be stiff and strong where it is joined or screwed into the bone but to have more flexible or elastic properties in a section that spans a fracture so as to more closely mimic properties of the bone and to permit load to be carried through the rejoined fracture sight.

Typically, primary fixation is achieved utilizing pins, screws, nails, porous surfaces, spikes or riveted fixation mechanisms. Plates and nails of joining implants act as internal fixation and alignment mechanisms for fracture segments. By designing the bone joining implant to vary materials, cross-sections, openings and other features, the implant may provide specific stiffness and stability to the fracture.

It would be desirable to manufacture a composite bone joining implant with material combinations in the same component of the implant. The value of such implants would be enhanced if they were complementary to the biomechanical features of the bone being joined or the joint being secured.

SUMMARY

In a first embodiment, provided are methods of fabricating a component, the methods including depositing a first layer of curable powder onto a platform disposed in a bore defined by a guide having an outer surface so as to define a depth between the platform and the outer surface; solidifying at least a portion of a first layer of curable powder so as to define a first solid region; effecting relative motion between the platform and the outer surface so as to increase the depth between the platform and the outer surface; depositing a second layer of curable powder onto the first solid region; and solidifying at least a portion of the second layer onto the first solid region so as to define a second solid region.

Also provided are fabrication systems. The systems suitably include a guide having an outer surface and defining a guide bore; a platform having an upper surface, the platform disposed within the bore and being movable in the bore relative to the guide; a feed container adapted to contain a powder; a transfer device configured to transfer powdered material from the feed container to the guide bore; a powder removal device configured to remove powder from the vertically-moveable platform; and a source of radiation configured to apply radiation toward the platform.

Further provided are implants configured to be attached to an underlying bone so as to provide stability to the underlying bone, the implants comprising a first region configured to be attached to the underlying bone; and a second region disposed adjacent the first region, the second region having a flexibility greater than that of the first region, and the second region being integral with the first region.

BRIEF DESCRIPTION OF THE DRAWINGS

The foregoing summary, as well as the following detailed description of preferred embodiments of the implant and method of the present application, will be better understood when read in conjunction with the appended drawings. For the purposes of illustrating the integrated multi-material implant of the present application, there are shown in the drawings preferred embodiments. It should be understood, however, that the application is not limited to the precise arrangements and instrumentalities shown. In the drawings.

DETAILED DESCRIPTION OF ILLUSTRATIVE EMBODIMENTS

Figure 1A:
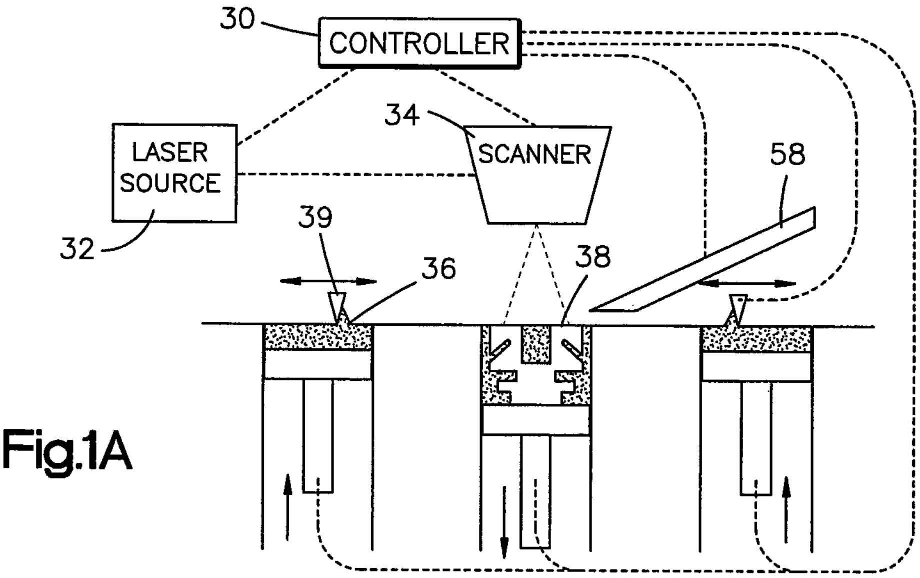
FIGS. 1A-1B illustrate several side elevation and top plan views of a manufacturing process utilized to construct implants in accordance with one embodiment.

It is to be understood that the present invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges includes each and every value within that range.

Certain terminology is used in the following description for convenience only and is not limiting. The words "right", "left", "top" and "bottom" designate directions in the drawings to which reference is made. The words "inwardly" and "outwardly" refer to directions toward and away from, respectively, the geometric center of the device and designated parts thereof. The words, "anterior", "posterior", "superior", "inferior", "lateral", "medial", "sagittal", "axial", "coronal," "cranial," "caudal" and related words and/or phrases designate preferred positions and orientations in the human body to which reference is made and are not meant to be limiting.

Certain terminology is used in the following description for convenience only and is not limiting. The words "right", "left", "lower" and "upper" designate directions in the drawings to which reference is made. The words "inwardly" or "distally" and "outwardly" or "proximally" refer to directions toward and away from, respectively, the patient's body, or the geometric center of the preferred implants and related parts thereof. The words, "anterior", "posterior", "superior," "inferior", "lateral" and related words and/or phrases designate preferred positions, directions and/or orientations in the human body to which reference is made and are not meant to be limiting. The terminology includes the above-listed words, derivatives thereof and words of similar import.

Figure 4A:
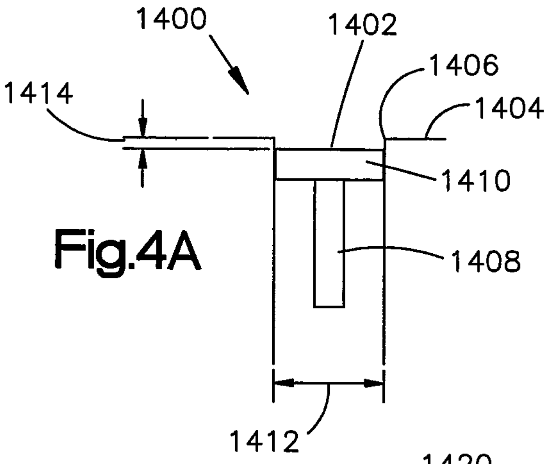
FIGS. 4A-4Y illustrate a non-limiting embodiment of a manufacturing method.
Figure 4B:
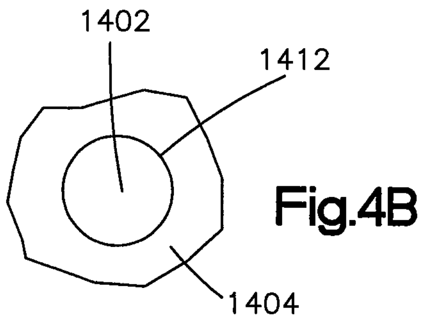

First provided are methods of fabricating a component. Reference is first made to exemplary FIGS. 4A-4Y to describe these methods.

The user may deposit a first layer of curable powder 1420 onto a platform 1410 (e.g., a piston) disposed in a guide bore 1412 defined by a guide 1404 having an outer surface 1406 (which may also be characterized as an upper surface, a rim, or an edge) so as to define a depth 1414 between the platform 1410 and the outer surface 1406. As shown in the appended figures, one may deposit a first layer of curable powder (suitably comprising a plurality of particles) onto the platform, and solidify at least a portion of a first layer of curable powder so as to define a first solid region. The user may effect relative motion between the platform and the outer surface so as to increase the depth or distance between the platform and the outer surface, deposit a second layer of curable powder onto the first solid region; and solidify at least a portion of the second layer onto the first solid region so as to define a second solid region. The methods will be explained first by reference first to non-limiting FIGS. 4A and 4B.

These figures show a device 1400, which device includes a platform 1410 having an outer surface 1402 (which may also be described as an upper surface) is disposed in the guide 1404, the guide defining a bore 1412 and an outer surface 1404, the outer surface having an edge 1406. In this non-limiting embodiment, the platform 1410 may be characterized as a piston, which piston has a rod 1406 that may be used to move the platform 1410.

The platform may be moved by application of mechanical, electromechanical, hydraulic, or even magnetic force. Ways to move the platform will be well-known in the art. The edges of the platform 1410 are suitably close-fit or sealed (e.g., via a gasket) to the bore 1412. As shown in the figure, the outer surface 1402 of the platform may be positioned at a distance 1414 below the edge or rim 1406 of the piston assembly. In some embodiments, the outer surface 1404 of the guide 1404 is characterized as an upper surface.

The guide may include a rim, 1406, which may be considered as part of the outer surface 1404. While round platforms are used to illustrate the claimed invention, there is no requirement that the platform have a round face. Platforms may be round, square, or polygonal in configuration.

The platform may be capable of being positioned beyond the outer surface 1406 of the guide 1404. The platform may also be capable of being positioned such that material disposed atop the surface 1402 of the platform 1410 is exposed beyond the outer surface 1406 of the guide 1404. As will be described elsewhere herein, this exposure allows the user to brush away excess material that may be atop or supported by the platform 1410, as shown in FIGS. 4P (removal of excess powder by brush 1460) and 4Q (removal of excess powder by vacuum 1470).

Figure 4C:
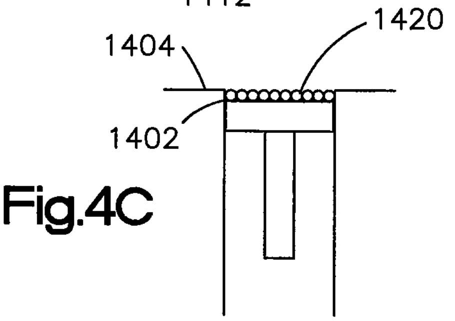
Figure 4D:
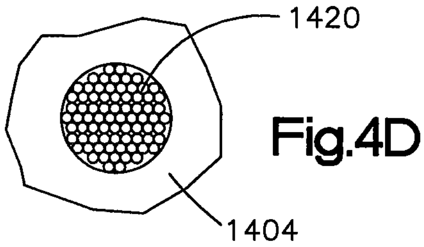

Deposition of a first curable powder layer is shown in FIGS. 4C and 4D. As shown in those figures, a layer of powder 1420 is deposited atop the upper surface 1402 of the platform. The layer of powder suitably has a height that is approximately equal to the thickness of one of the particles of the curable powder of the first layer, although the layer may be thicker. As shown in FIG. 4D, the powder layer may cover essentially the entirety of the upper face 1402 of the platform, although complete coverage is not a requirement.

Suitable powders include virtually any curable material. Powders of polymers, metals, and the like are all considered suitable. A layer of powder may be of an essentially monodisperse powder or of a polydisperse powder. For example, a layer of powder might include a monodisperse population of PEEK particles. The first, second, or both layers of powder may be monodisperse or polydisperse—any layer of powder may be mono- or polydisperse. Any layer of powder may also include a mixture of two materials (e.g., two kinds of polymer).

Alternatively, the layer might include PEEK particles of various sizes/dimensions. A layer might include particles of two different kinds of materials, e.g., PEEK and a metal. Particles may thus differ from one another in terms of size, material, or both. Polymer particles, such as those of PEEK, polyethylene, and the like are considered especially suitable. Metallic particles, such as stainless steel, are also suitable.

Powder can be of virtually any material. A non-limiting list of powder materials includes: steel (conventional and stainless), steel alloy, aluminum, titanium (and alloys thereof), PEEK, polyethylene, other polymers, and the like. A given particle may itself comprise one, two, or more materials. For example, a given particle may itself be a mixture of two or polymers, metals, or both. For example, a single particle may itself be a mixture or alloy or two metals. Materials that are capable of melting or being welded together are considered especially suitable. The grain size of a suitable powder material is in the range of from about 0.005 mm or even about 0.01 mm to about 0.1 mm, 0.5 mm, or even 1 mm or 2 mm. The grain size distribution may be set by the user according to the user's needs.

The user may also perform a selective melting application. In the exemplary case of PEEK, the process chamber and powder are to heated close to PEEK's melting point (e.g. 350 degrees), the beam will only introduce the final amount of energy required to induce the melting of the PEEK. Variations of this approach may be applied to a variety of materials in addition to PEEK. For example, a user may apply a particular temperature for a particular duration so as to solidify only some of an applied powder. In this way, the user may selectively melt (so as to later solidify) or fuse only a portion of the material being processed. For example, the user might heat the workspace to a temperature sufficient to solidify a polymer powder that has been applied but not a metal powder that has been applied.

The optimal conditions to process a particular kind of powder will depend on the powder and on the user's needs. For PEEK powder, energy of about 40 W, a scan velocity of about 1500 mm/s, and a focus of about 0.1 mm diameter is considered suitable. For steel powder, a power of 200 W, a scan velocity of about 1000 mm/s, and a focus of about 0.15 mm diameter is considered suitable. The optimal power application will depend on the user's needs and on the characteristics of the materials being processed. It is considered suitable (but not necessary) to have a first solidified layer cool before forming a second layer atop the first layer. In practice, the first layer solidifies long before the second layer is applied and processed.

A given layer of powder may include two kinds of particles, which particles may be of different materials. The weight ratio of two materials in a layer may be from about 10,000:1 to about 1:10,000, or from about 1000:1 to about 1:1000, or from about 10:1 to about 1:10, or even about 1:1. The optimal ratio of one material to another will depend on the needs of the user; a given powder layer may include two, three, four, or more different materials. The number ratio of differently-sized particles in a layer (e.g., in a layer that includes particles of different sizes) can be virtually any ratio.

In some embodiments, the first layer 1420 is an initial layer, such that the first depositing step comprises placing the first layer directly onto the platform. In other configurations, the first layer 1420 is deposited onto a previously-solidified solid region supported by the platform.

Figure 4E:
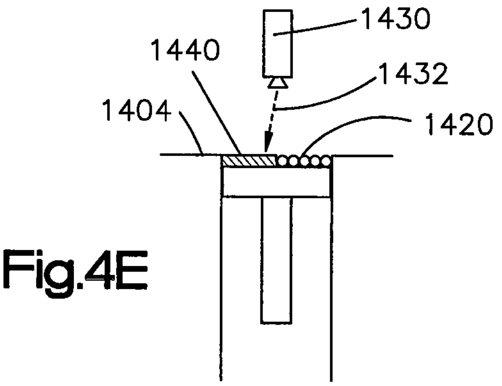
Figure 4F:
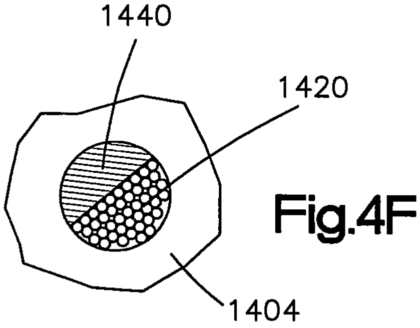
Figure 4G:
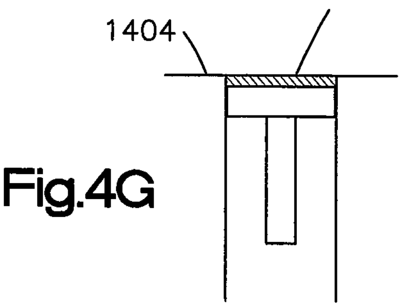
Figure 4H:
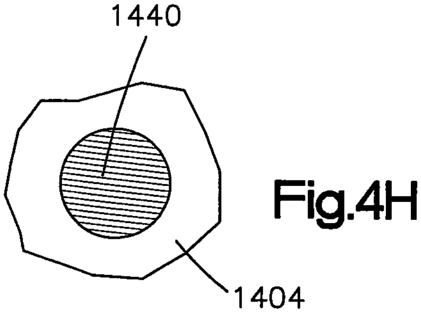

FIGS. 4E and 4F illustrate solidifying at least a portion of a first layer of curable powder so as to define a first solid region. The solidification is suitably effected by application of energy (e.g., radiation) 1432 from a source 1430 to at least a portion of first powder layer 1420. The application of the energy suitably renders a portion of that layer 1420 into a first solid region 1440. The source of energy may be a laser, a maser, a source of infrared radiation, a source of ultraviolet radiation, or other radiation capable of curing the powder. The user may also use a heated fluid (e.g., a gas) as a source of energy. A heated object (such as a heated plate, stylus, or patterned stamp) may also be used as a suitable energy source. Electron beams, plasma beams, protons, or other particle beams are also suitable energy sources. Ultrasound may also be applied to modulate or otherwise affect melting and solidification; vibrational energy or force may be applied to remove powder that has not solidified. As shown in FIG. 4F, the user may solidify 1440 only a portion of the first powder layer 1420.

The user may solidify the powder into virtually any pattern—as described elsewhere herein, the user may effect a particular solidification patter by effecting relative movement between the radiation source and the layer of powder. For example, the source 32 may be moved to a particular location above the platform 1410, and then apply radiation 1432 to material supported by the platform. The source 1432 may apply radiation while moving between two or more locations so as to effect a line of solidified powder.

In an alternative embodiment, the source 1432 remains stationary, and the platform 1410 is moved relative to the source. The user may also move both the source 32 and the platform 1410 relative to one another. The source may translate in the x-y plane, and may also move in the z-axis. The source may be configured so as to apply radiation perpendicular to the surface 1402 of the piston 1410; the source may also apply radiation at an angle to the surface 1402.

The user may also effect a solidification pattern by interposing a mask between the radiation source and the layer of powder, or both. Application of radiation to the first powder layer may result in a layer of fully-solidified material 1440 from the curing of the first powder material.

The beam may be applied in a variety of ways. In some cases, a weld (i.e., a region of solidification) at the outer contour of a piece may be weakened by welds at the interior of the piece. An increased distance between outer and inner welds may improves processability of inclinations within a body, and welding the outer contours after the inner welds improves processability of inclinations. Sequential welding from the outside of a piece toward the interior of a piece also, in some embodiments, results in improved material properties. In some situations, if weld paths are not adjacent to each other, a narrow focus may produce a suboptimal growth of the welds sequentially placed one above the other. Similar effects occur at higher energy levels, even with weld paths close to each other.

Figure 4I:
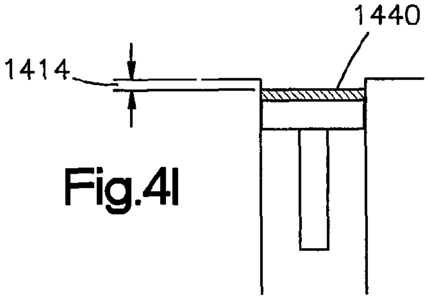
Figure 4J:
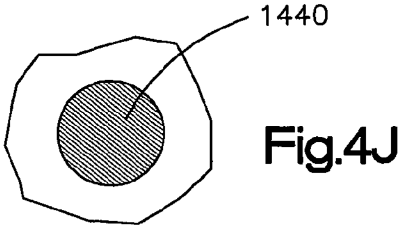

In some embodiments, the user may then effect relative motion between the platform and the outer surface of the guide, so as to increase the depth between the platform and the outer surface. This is shown in FIGS. 4I and 4J, which figure illustrates that relative motion between the platform and the guide (not labeled) gives rise to a distance 1414 between the outer surface of the guide and the top surface of the solid material 1440. The relative motion may be effected by moving the platform 1410 relative to the guide 1404, by moving the guide 1404 relative to the platform 1410, or both.

Figure 4K:
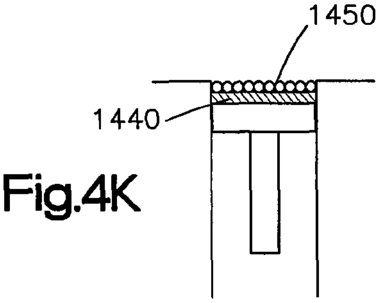
Figure 4L:
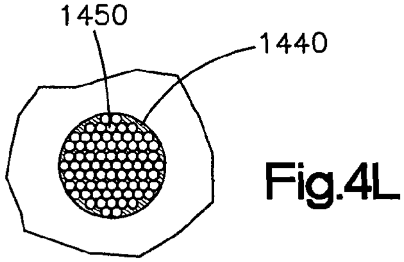

The user may then deposit a second layer of curable powder onto the first solid region. This is illustrated by FIG. 4K. As shown in that figure, a second layer of curable powder 1450 is deposited atop the first solid region 1440. The thickness of the second layer of curable powder is suitably about equal to the thickness of one of the particles of the curable powder of the second layer, although the layer may be thicker than that.

In one embodiment, the distance 1414 between the outer surface of the guide and the upper surface of the solid material 1440 is approximately equal to (or slightly greater than) the thickness of one of the particles of the curable powder of the second layer; in this way, after second curable powder may be applied to the recessed solid material 1440, excess second powder may be removed by application of a sweeper or wiper (not shown), which leaves behind a layer of second powder that has a height of the distance 1414.

In such embodiments, once the user solidifies a layer of curable powder (which layer could be the first or initial layer of powder), the user may advance the platform upwards. This may be done so as to raise the region of solidified powder upwards so that the user can remove any uncured or excess powder by brushing, vacuuming, by precipitating, or by other methods of removing or collecting powder or particulate matter.

The platform may be raised by an amount sufficient (e.g., by about the height of the layer of powder that was solidified) so as to expose essentially only the solidified region of powder above the rim of the piston bore. A generally 0.03 mm to 0.1 mm thick layer of powder is achieved by moving the area to be processed downwards by this amount and then applying the powder (as shown by FIGS. 4G, 4I, and 4K), although powder layers of less than 0.03 mm and more than 0.1 mm can be formed, by appropriate choice of powder size and by appropriate modulation of the platform's movement. The optimal thickness of a powder layer may depend on the needs and processing constraints of the user, and powder layers may be in the range of fractions of millimeters, into the millimeter range.

Figure 4M:
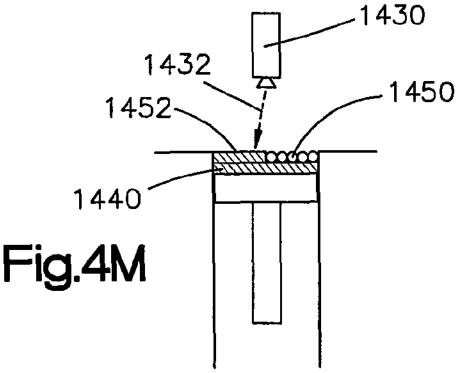
Figure 4N:
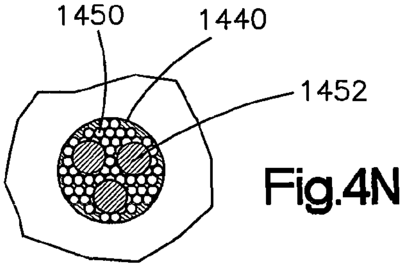

The user may then, as shown in FIGS. 4M and 4N, solidify at least a portion of the second layer onto the first solid region so as to define a second solid region. This solidification is suitably accomplished by application of radiation 1432 from a source 1430 to the second layer 1450. The radiation then converts at least a portion of the second layer 1450 to a second solid region 1452 atop the first solid region 1440. As shown in the top view of FIG. 4N, the solidification may be performed so as to give rise to discrete solidified regions 1452 of the second powder atop the solidified first region 1440. Unsolidified particles of the second powder 1452 may remain atop the first solid region 1440. The solidifying may fuse the second solid region and first solid region; such fusion may be characterized in some embodiments as sintering or even as welding. In some embodiments, adjacent layers of powder bind to each other. This may occur where the adjacent layers are of the same or similar materials. Materials may also be chosen such that parts of one material layer diffuse into an adjacent layer.

In some embodiments, portions of one adjacent layer may become physically integrated into the adjacent layer. This may occur where a first layer is porous or has a surface roughness and portions of the second layer become integrated with those features of the first layer. As shown in the appended figures, e.g., FIG. 16A, layers of material may also be constructed such one region 1202 is fit together with another region 1204.

The user may solidify powder in virtually any pattern; the columnar regions shown in FIG. 4N are illustrative only. Solidified regions may be circular, polygonal, square, or other shape. In one variation, the user may solidify an O-shaped ring of powder and remove the unsolidified powder at the center of that ring. The user may then construct additional O-shaped rings atop the first ring to give rise to a hollow column. The interior of the column may then be filled with a liquid or other material, if desired.

The invention may also be used to create bodies that include internal void spaces. One way to effect such voids is to solidify a first layer of powder. Atop that layer, the user then solidifies a second layer of powder, but leaves several holes in the second layer. The user may then remove the workpiece and then place that workpiece, face-down, atop another solid layer of material, and continue constructing the device. The holes in the second layer are then rendered capped, resulting in a body that has voids disposed within.

A workpiece (i.e., a body made of solidified powder) may be moved, rotated, or otherwise manipulated during processing (not shown). In this way, a user may create a body with virtually any feature extending in virtually any orientation. For example, a user might construct a cubic body by solidifying successive layers of one or more powder materials. The user may then construct a protrusion (e.g., a spike) that extends from a first face of the cube. The user may then rotate the workpiece and construct a second protrusion from another face of the cube (not shown).

Placing voids in a body may be useful to confer a particular physical property on the body, as voids present in the body may give rise to a body that is less rigid and is more flexible. The voids may also be used to contain an agent or drug so as to store such material within the body. The voids may also be used to contain a material—such as monomer—that may be cured at a later time. For example, such an implant may be introduced to the body, following which introduction monomer disposed within the implant may be solidified by application of an appropriate energy. A body may also include a region (typically internal) that comprises unsolidified powder. Such bodies may be implanted, and the unsolidified powder within the body may be solidified at a later time by application of appropriate radiation.

The user may also, by leaving unsolidified regions at the edges of the layers that make up the body, give rise to a body with a surface that is pitted, porous, roughened, or otherwise featured. Such surfaces may be used to promote in-growth of bone, or other tissue. Such surfaces may also be coated, as coatings may exhibit improved coverage or adhesion to a non-uniform surface.

Figure 4O:
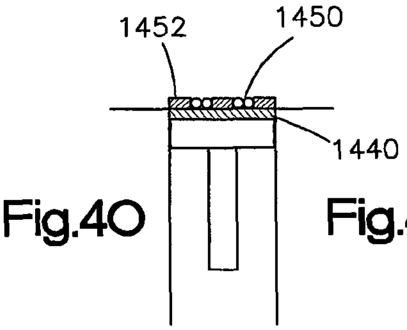
Figure 4P:
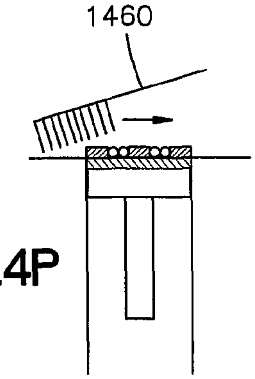
Figure 4Q:
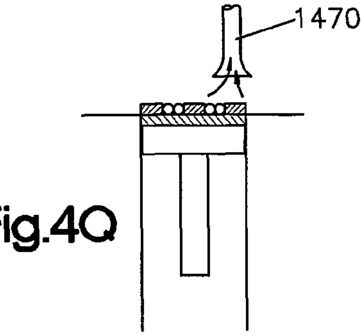

After solidification, the piston may then be moved upwards, as shown in FIG. 4O. This may be done so as to bring the unsolidified powder 1450 from the second powder layer up to a location where the powder may be swept, vacuumed, brushed, blown, or otherwise removed form the workpiece, as shown in FIGS. 4O, 4P, and 4Q. Powder is suitably removed after formation of a solidified region of material; removing the powder then defines a first, second, or other solid region.

As described elsewhere herein, relative motion between the platform and the outer surface may elevate the first solid region, the second solid region, or both (or any other solid region), beyond the outer surface or even with the outer surface. In FIG. 4P, there are regions of powder 1450 between solidified regions 1452. The piston has been advanced upward such that the powder 1450 is exposed above the surface of the guide. A brush 1460 or vacuum 1470 may be used to remove excess powder 1450. The user may also use static electricity, a blower, or other suitable methods of removing powder.

Figure 4R:
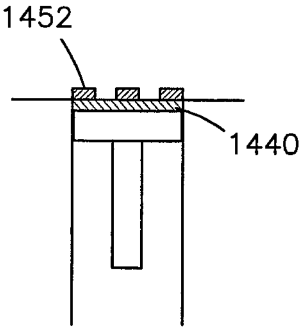
Figure 4S:
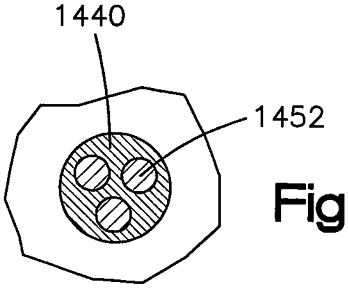

FIG. 4R illustrates solidified regions 1452 atop a second solidified region 1440, with excess powder (not shown) removed. FIG. 4*s* illustrates a downward view of the solidified regions 1452.

Figure 4T:
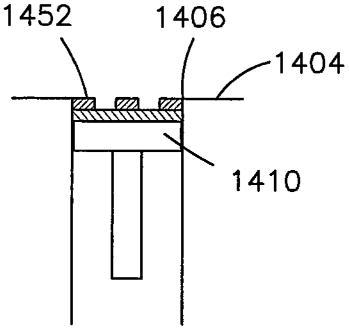
Figure 4U:
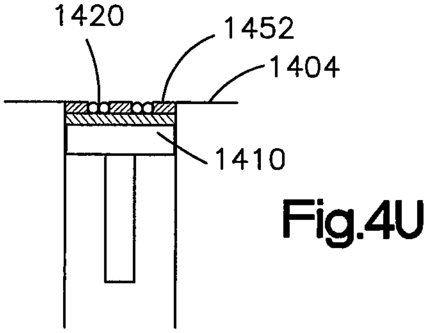
Figure 4V:
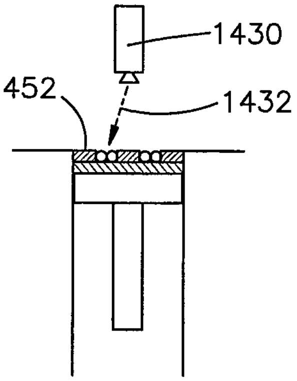

The piston face may then be translated downwards, as shown in FIG. 4T, such that the tops of the solid structures are essentially flush (i.e., even) with the edge 1406 of the bore. A third layer of powder (as shown in FIG. 4U) may then be introduced so as to fill in the spaces between the solidified regions 1452. This is shown by FIG. 4T, which illustrates the third layer of powder filling in these spaces. (The leveling of the third layer of powder 1420 is not shown.) Further layers of powder (not shown) may be applied and processed; these layers may be stored in their own separate containers.

The third layer of powder is then solidified by application of energy 1432 from an energy source 1430. This gives rise to the solidified regions 1452 of the second material being effectively embedded in a layer 1440*a* of the solidified third powder. In this illustration, the powders in the first and third layers are the same; there is no requirement, however, that any two layers of a body be the same.

Figure 4W:
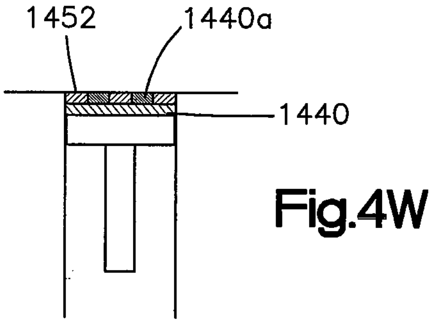
Figure 4X:
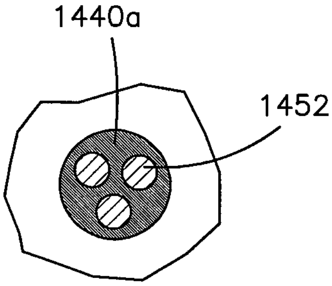
Figure 4Y:
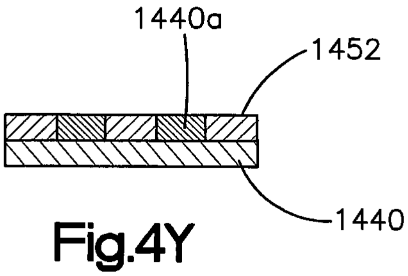

This is shown also in FIG. 4X, which illustrates a downward-looking view of solidified regions 1452 residing in a solidified layer 1440*a*. 4Y is a cutaway view of the body made in FIG. 4W, showing the first layer 1440, the solidified regions of the second material 1452, and the layer of material 1440*a* in which the solidified second material 1452 is disposed.

Powder may be provided from feed containers. In a process that uses multiple materials, each material may be stored in a separate feed container. For example, a first powder might be stored in a first feed container, and a second powder (e.g., a material used for an additional layer of powder) is stored in a second container. Additional powders may be stored in their own containers (e.g., a third powder is stored in a third feed container, a fourth powder is stored in a fourth feed container, and so on). A feed container may be disposed proximate to the guide.

Figure 1B:
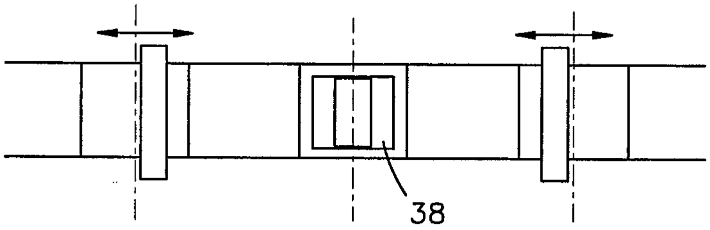
Figure 2A:
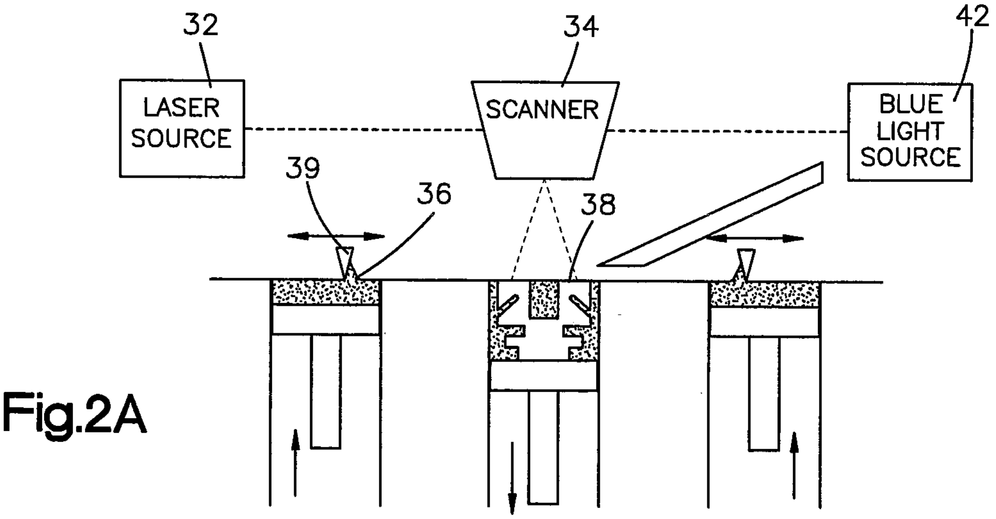
FIGS. 2A-2B illustrate various views of a manufacturing mechanism and materials storage device.
Figure 2B:
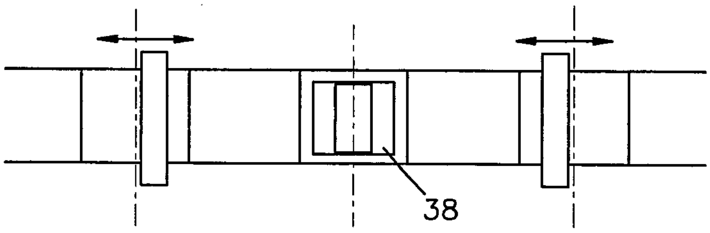
Figure 3A:
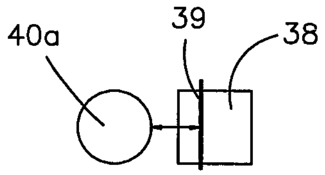
FIGS. 3A-3D illustrate various views of a manufacturing mechanism and materials storage device.
Figure 3B:
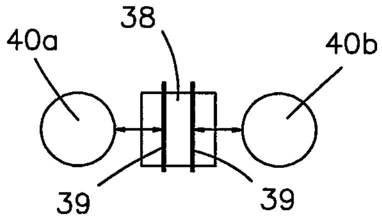
Figure 3C:
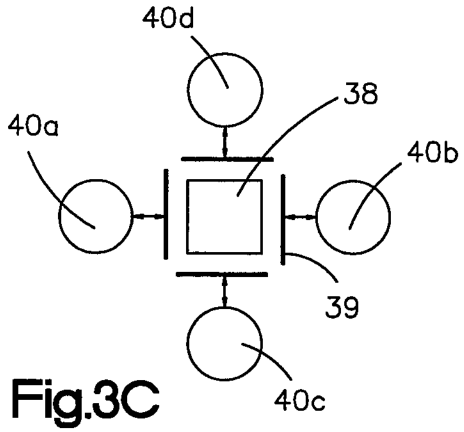
Figure 3D:
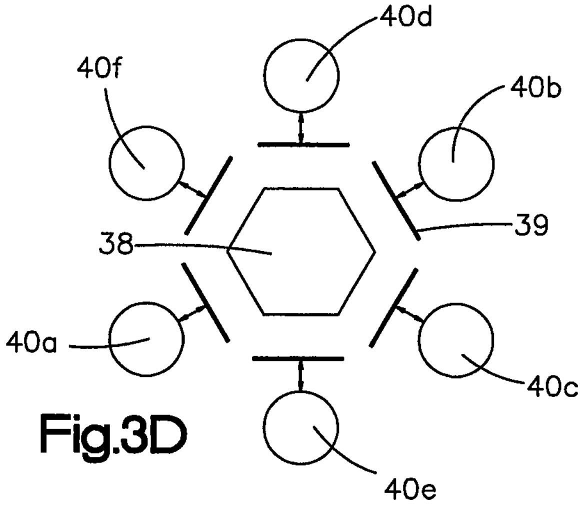

Reference is now made to FIGS. 1, 2, and 3, which illustrate an embodiment wherein selective laser sintering process or a similar process may be utilized to manufacture various implants and other bodies, including those described elsewhere herein.

With reference to FIG. 1, the process is generally comprised of an additive, rapid manufacturing technique that uses a source 32 (e.g., a laser) to fuse particles of material, such as plastic, metal or ceramic powders, into a mass representing a desired 3-dimensional object.

An energy (e.g., radiation) source 32 (e.g., a laser) fuses the powdered material 36 by scanning cross-sections of the part generated by a controller 30 utilizing a scanner 34 at the surface of a powder bed 38. After each cross section of the part is scanned by the scanner 34, the powder bed 38 is lowered by one thickness, a new layer of powdered material is added to the top of the powder bed by powder application device 39 and the process is repeated until the part is completed. Although a laser is described here, other sources of radiation or energy may also be used to solidify the powder. A pusher 58 may also be used to assist with applying or removing powder. The system may also include a controller that modulates the application of the radiation (e.g., by modulating the movement of the radiation source, by using a mask to effect a pattern of radiation application, by moving the workpiece, or any of these).

The controller may apply radiation to one or more predetermined locations. As described elsewhere herein, the user may have a need for a body or part of a particular configuration. The user may then create a sequence of powder application and powder solidification steps to give rise to the desired part. The user may then configure or otherwise program the system to execute a particular sequence of steps to fabricate the desired part. As part of this program, the system may apply radiation to one or more preselected or predetermined locations. The system may also apply preselected amounts and types of powder, in concert with the radiation or energy application.

Two or more materials may be combined by selectively placing powders in the powder bed 38 or fusing a first material at the powdered bed 38, removing the powder of the material from the specific layer, applying a second material powder to the layer and fusing the powder of the second material at the specific layer based upon the guidance of the controller 30. The powdered materials are preferably stored or maintained in hoppers 40*a-e* (see FIG. 3) with the number of hoppers corresponding to the number of materials desired to be used in any particular component. A hopper may contain a single material or even a mixture of materials.

When removing material, specifically the powdered material 36 from the powder bed 38 following an initial scan of the powdered bed 38 by the scanner 34, the powdered material 36 may be removed by vacuum, sweeper, electrostatic cleaner, blower, wiper, or by nearly any other mechanism that removes excess powdered material 36 from the powder bed 38 to facilitate processing of the next layer of powdered material 36.

One embodiment involves depositing a first powdered material 36 onto the powder bed 38 and filling a second portion of the powder bed 38 with a second powdered material 36 at portions of the cross section where the second material is incorporated in the component design. The controller 30 directs the laser source 32 and the scanner 34 to fuse the desperate materials 36 into a three-dimensional layer of material that corresponds to the specific layer of the component.

A new layer with the different materials 36 is deposited on top of the fused layer and the process is repeated until the final part is manufactured. A scanner may be used to assess the condition of powdered material disposed on the powder bed 38 (within the guide bore), which condition may in turn be used to modulate application of radiation, ions, or other energy to the powder. As shown in the figure, the powder may be supplied from two hoppers; two, three, or even more hoppers may also be used. An embodiment having a single powder source (e.g., hopper) is also suitable.

In the non-limiting FIGS. 1 and 2, powder supply platforms (which may be configured as pistons) are disposed at about the same height as the powder bed. In such a configuration, powder is supplied from the supply piston and is then swept or otherwise transferred over to the powder bed 38 for processing. This is not a requirement, as powder may be supplied from a source disposed above the hopper. In such an embodiment, powder is dispensed adjacent to the powder bed and is then transferred to the powder bed, e.g., with a blade, scoop, sprayer, wiper, and the like. The powder may also be dispensed at a distance (e.g., millimeters, centimeters) from the powder bed and then delivered to the powder bed.

A device for spreading powder to the working platform and also devices for removing excess powder are also suitably present. In one embodiment, the system includes a blade (or scraper) 39 that deposits a powder in front of the wiper, which wiper may be in the form of a blade, in the form of a brush, or even a blade and brush. The deposition may be from a single, independent container, or from a single container that is part of a group (e.g., a row) of other containers, each containing a different powdered material. The system may be configured to dispense only one powder in advance of the wiper, or to dispense more than one powder in front of the wiper. The wiper may also be used to remove excess or unwanted powder. While certain of the figures illustrate spreading powder across the entirety of the platform or across the entirety of another supporting layer, this is not a requirement. A user may spread powder across only a portion of the platform or a supporting layer, and systems may be configured so as to effect this type of spreading.

As described elsewhere herein, ultrasonic or other vibrations may be used to give rise to an even layer of the powder. It is considered suitable to ensure that powder is present at the edge or rim of the guide; if insufficient powder is present at the rim subsequent application of energy may only heat the rim and may not heat adjacent powder because there was no powder to absorb the heat. Thus, robust powder distribution is helpful in executing these methods. Alternatively, having a comparatively high temperature in the process chamber may reduce temperature gradients within the material being processed; for example, a user might apply powder and wait for the powder to achieve a particular temperature before processing the powder. Users may also account for the changes in cross-section as different layers of a piece are constructed, as the energy required to process a first layer of powder may differ from the energy required to process a second layer powder (adjacent to the first) that may be of a different cross-section or even a different material than the first layer.

Powder may also be injected or sprayed into the atmosphere of the process chamber and then allowed to fall (e.g., like snow) onto the area to be processed. In other embodiments, powder may be dispersed onto a conveyor belt for dispersion onto the working platform. The belt may be moved within the process chamber, while distributing the powder.

Referring specifically to FIG. 2A, certain powdered materials 36 may be inappropriate for processing with a typical laser source 32 and the scanner 34. Such sensitive powdered materials 36 may be fused or processed using a lower energy mechanism, such as a blue light source or other light source 42. In such a configuration, the controller 30 (not included in FIG. 2 for clarity purposes) directs the laser source 32, scanner 34 and/or blue light source 42 to fuse or process the desperate materials deposited via deposition device 39 on the powder bed 38, depending upon which material is being processed.

The deposition device may be a bar, blade, or wiper that is moved to as to transfer powder to the powder bed 38. The manufacture may entail the use of two or more different energies to solidify powders. For example, a system may use a first type of energy (e.g., laser radiation at a first wavelength) to fuse a first type of powder, and then use a second type of energy (laser radiation at a second wavelength) to solidify a second type of powder. The energy source may be adjustable; a system may also instead include multiple energy sources.

In some embodiments, a high powered laser source 32 is typically utilized to fuse the material when a metal or ceramic powder 36 is processed and the blue light source 42 may be utilized when a more sensitive material, such as a polymeric powdered material is processed. The blue light source 42 is not limited and may be comprised of nearly any light sources such as ultraviolet or infrared light sources that fuse or process specific powdered materials to form the final component. In addition, electrostatic deposition of powdered materials may be utilized to process the components.

As shown in FIGS. 1 and 2, the hopper or powder containers may be pistons that are adjacent or nearby to the powder bed 38 (also referred to as a platform). The tops of the bores in which the powder container pistons are placed may, as shown in FIG. 1, be level or essentially planar with the top of the bore in which the powder bed (or platform) is disposed. This allows the user to sweep, blow, or otherwise transfer powder from a powder container onto the powder bed.

The systems shown in FIGS. 1 and 2 may be configured to operate in a concerted manner, wherein while the system is solidifying a given amount of powder on the powder bed so as to form a solid region, the platform within a powder container corresponding to the next layer of powder to be applied to the platform is moving so as to present the desired quantity of powder to the powder transfer device. In this way, the system readies the next amount of powder for delivery as the previous amount of powder is being processed on the powder bed. As described elsewhere herein, powder may transferred to the powder bed by a device that also removes excess powder from the bed following a solidification step.

As one example of these concerted processes, a first hopper may dispense powder that is then distributed to the powder bed (platform) 38. While the powder atop the powder bed is solidified, a second hopper readies a second powder for distribution to the powder bed. Excess powder is removed from the powder bed 38 following solidification, the powder bed is incremented by a distance such that the second powder may be distributed atop the solidified first powder to form a single-particle thickness layer.

Referring to FIG. 3, multiple hoppers 40*a*-40*f* are utilized to store desperate powdered materials 36 for deposition on the powder bed 38 for processing. The hoppers 40*a*-40*f* may be utilized to store blended materials for transition areas, highly elastic materials, metallic powders for forming rigid or stiff portions of a body, or nearly any materials that permit adaptability and manufacturing of the desired products. A blade 39 or other device (e.g., wiper, scraper) is suitably used to transfer powder to the powder bed. Feed containers may be disposed in virtually any position relative to one another; they may be next to one another, or even opposite to one another.

The powder bed may be dimensioned to as to meet the user's needs. The bed may have a width in the range of millimeters, centimeters, or even larger; exemplary beds have a cross-sectional dimension (e.g., width) in the range of from about 10 mm to about 500 mm. The bed may be circular, polygonal, ovoid, or virtually any shape that the user may require. The bed may also include (not shown) inserts or overlays (in the manner of a cookier cutter or stencil) that mask a portion of the bed so as to change the cross-section of the platform. For example, a platform having a radius of about 1 cm may be overlaid by a doughnut-shaped stencil with a major radius of 1 cm and an inner "hole" radius of about 0.5 cm. The inner "hole" may be circular, square, or virtually any other shape.

Powder supply pistons and powder beds may be disposed in virtually any configuration. As shown in exemplary FIG. 3D, powder supply pistons 40*a*-40*f* may be disposed around the powder bed (or platform) 38. In other embodiments, a central powder supply piston may be surrounded by powder beds. A powder supply piston may be flanked by two powder beds such that a blade or wiper may operate in a reciprocating manner so as to deliver powder from the supply piston to the beds.

Figures 5A, 5B, 5C, 5D, 5E, 5F:
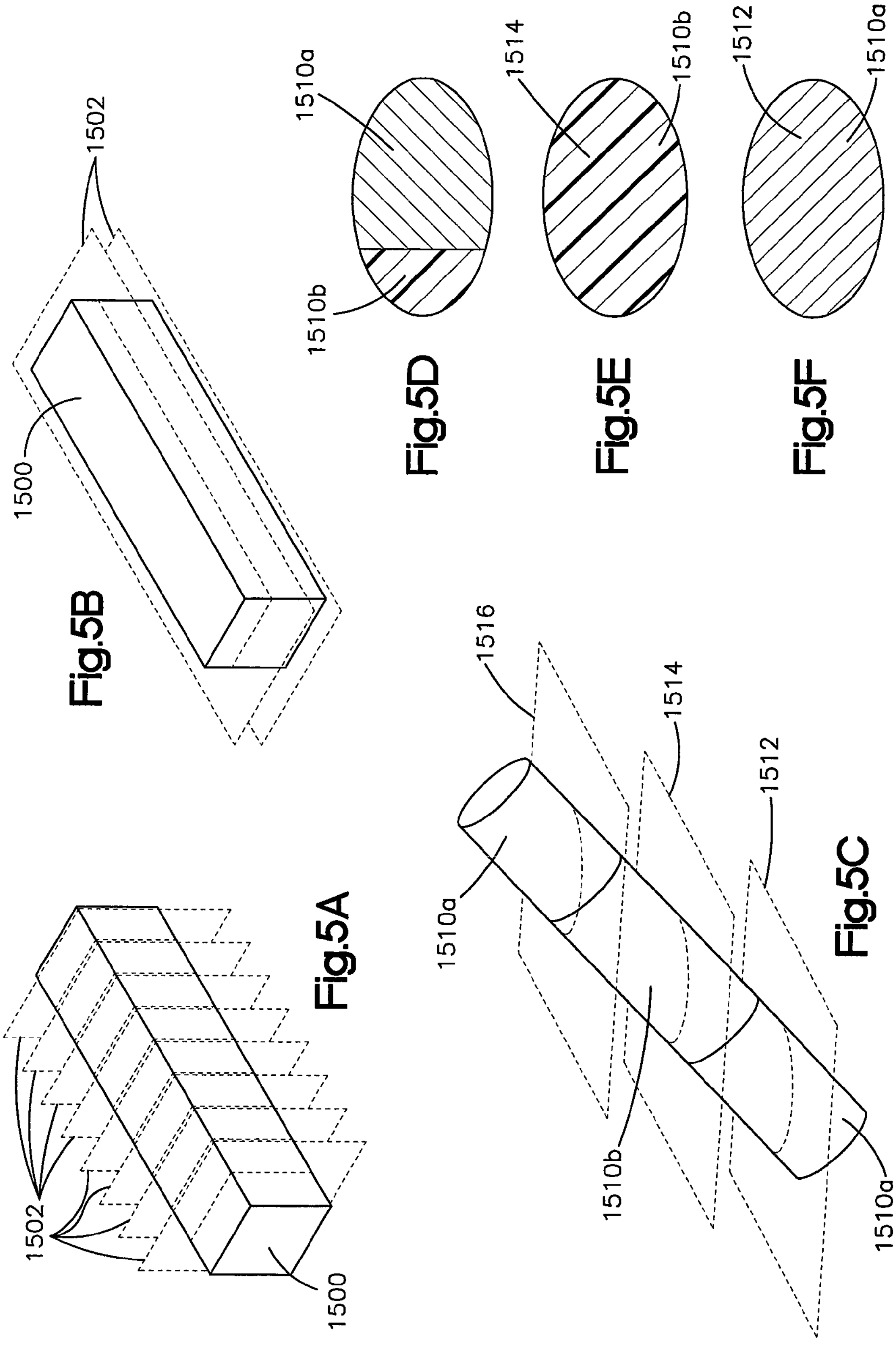
FIGS. 5A-5C illustrates alternative approaches to manufacture.
Figure 15A:
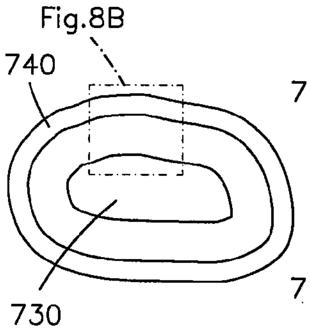
FIG. 15A illustrates a top plan view of a bone joining nucleus replacement device in accordance with a seventh preferred embodiment of the present application.

FIG. 5 illustrates various embodiments of the disclosed methods. In FIG. 15A, a body 1500 may be constructed or "built up" in slices 1502 from one end of the body to the other. This results in the production of the body by way of solidifying many, comparatively small slices. An alternative embodiment is shown in FIG. 5B, which figure depicts construction of a body 1500 from the bottom-up, using fewer, larger slices 1502. Constructing as in FIG. 5A may take additional time, as many individual slices must be constructed. Construction according to FIG. 5B may be faster, as fewer slices are needed, although larger slices may, in some cases, present more opportunity for variation. Thus, in some embodiments, construction of a piece that is oriented in vertical direction may be slower than construction of a piece that is oriented in a horizontal configuration. Process conditions and setting may be modified, however, according to the user's needs, and some users may find it suitable to construct vertically-oriented bodies more quickly than horizontally-oriented bodies.

FIG. 5C illustrates one embodiment wherein a part is formed at an angle. As shown in the figure, one may form layers 1512, 1514, 1516 of varying cross section along the length of the body to arrive at the final product. A first (lower) layer 1512 is comprised of a first material 1510*a*, e.g., a metal that confers rigidity to the body. A middle layer 1514 is comprised of plastic or other flexible material 1510*b* so as to confer some flexibility on the body. An upper layer 1516 may be formed with both materials 1510*b* and 1510*a*.

In this way, the methods allow for the creation of objects having a cross-section that may vary in size, material, or both. As described elsewhere herein, layers may have different cross-sectional areas from one another, which thus enables the user to build up a body at an angle, such as the body of FIG. 15C. Configurations that minimize the amount of contact area between the part being formed and the platform surface are considered especially suitable; methods that entail construction of successive, comparatively large layers may also be used.

Figure 6A:
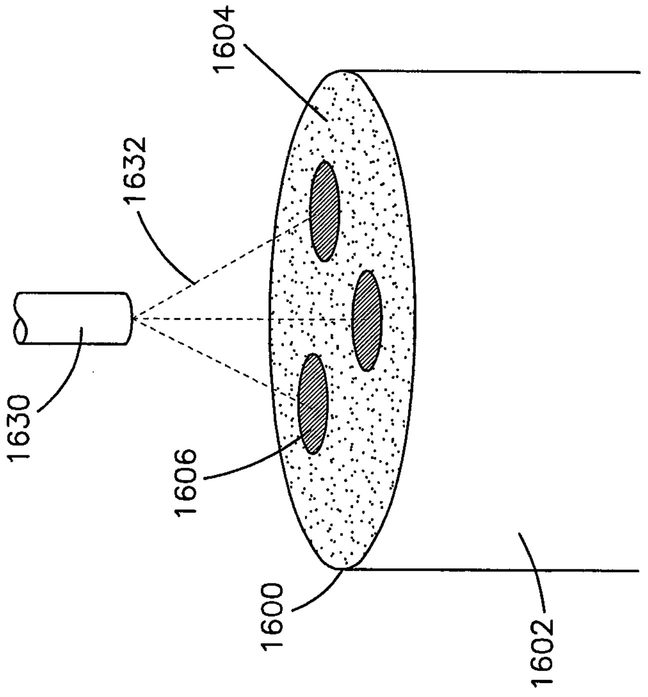
FIGS. 6A-6B illustrate alternative approaches to manufacture.
Figure 6B:
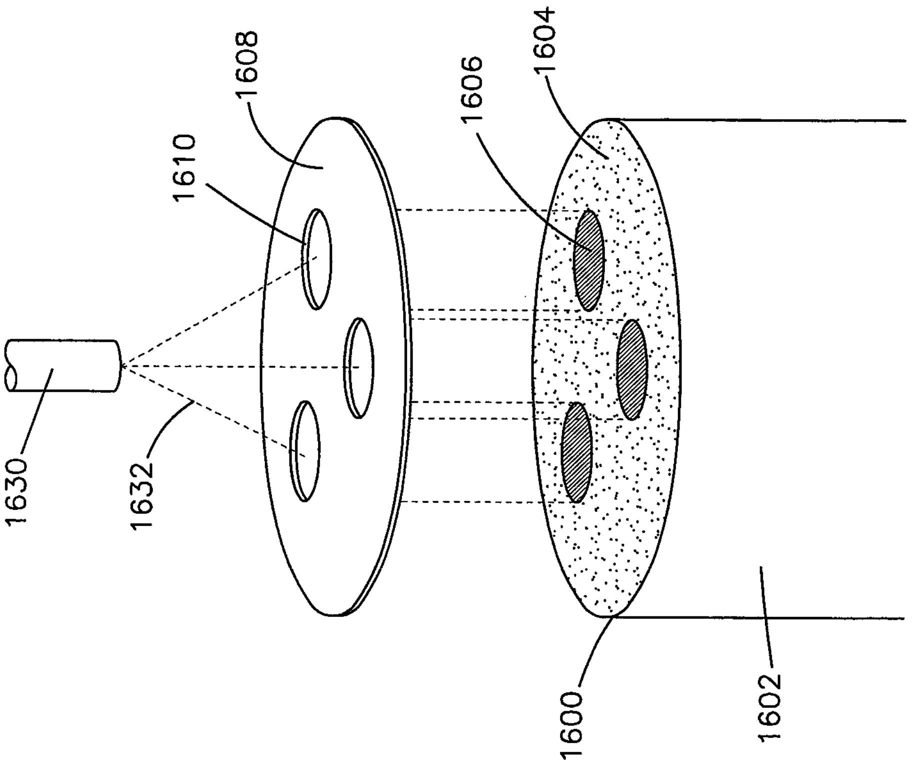

Exemplary methods of applying radiation are shown in FIGS. 6A and 6B. FIG. 6A illustrates the formation of solidified powder regions 1606 by moving a laser (or other radiation source) beam 1632 to various locations on the powder 1604 to solidify the desired regions. The energy may be applied in spots, bursts, lines, or other configurations. Alternatively, the energy may applied constantly while the beam is moved, so as to give rise to a solidified or welded line of material. The energy is suitably supplied by a device 1630, such as a laser, maser, or the like. The powder 1604 is disposed on the upper face 1600 of a piston 1602. The energy source is suitably capable of movement in at least one direction; sources that move in the x, y, and z-directions are suitable, as well as sources capable of tilting.

The user may also use a mask 1608 so as to direct radiation to only those desired locations, as shown in FIG. 6B. In that figure, a mask is disposed between the energy source and the target powder layer so as to effect illumination of only certain regions 1606 of the powder layer 1604. The mask may be patterned in virtually any way, which in turn allows the user to form virtually any pattern of solidified powder. The mask may have holes 1610, straight lines, curved lines, and the like formed within. The mask is, as shown, suitably opaque to the applied radiation. The mask is suitably capable of being positioned such that the apertures block at least a portion of radiation being applied by the source of radiation in the direction of the upper face of the moveable platform In some embodiments (not shown), the user may use a mask to assist with application of powder for subsequent processing. In this embodiment, a mask or stencil may be laid atop the surface that is to support a layer of powder. The user may then apply the powder, which will then cover only those parts of the surface that were not masked by the powder. The stencil may be of a thickness that is approximate to the single-particle thickness of a layer of the desired powder. In operation, the user then removes any excess powder and solidifies the remaining powder (this can be done with or without the stencil in place). The methods may form features of fine resolution. In some embodiments, features having a characteristic dimension of 0.05 mm and greater may be formed; finer features may also be produced.

Figure 7A:
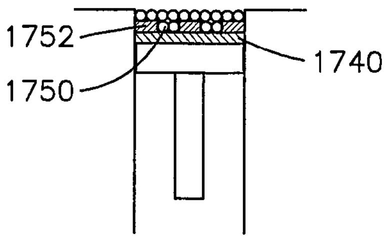
FIGS. 7A-7E illustrates one exemplary approach to manufacture.
Figure 7B:
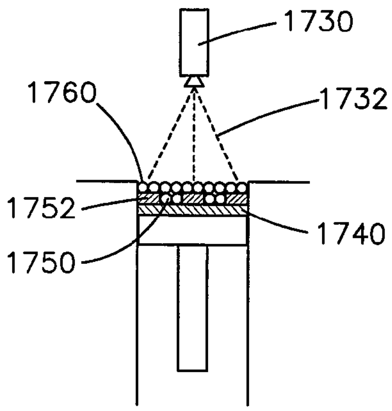
Figure 7C:
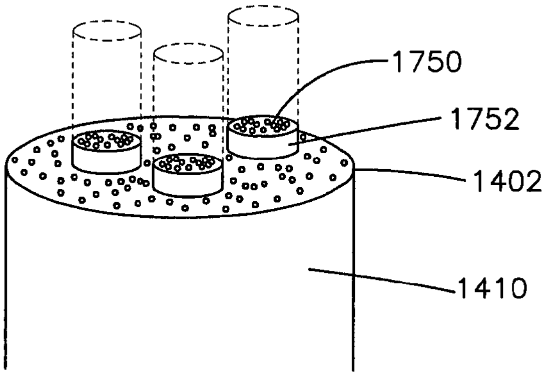
Figure 7D:
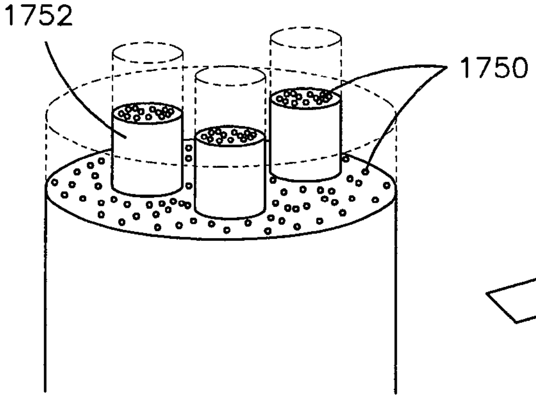
Figure 7E:
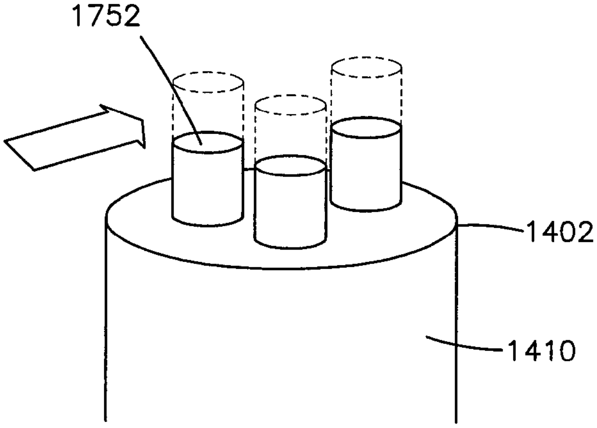

FIGS. 7A-7E illustrate another, non-limiting embodiment. FIG. 7*a* illustrates placement of powder atop a workpiece (similar to that of FIG. 4*r*). The powder 1750 is disposed atop the surface features 1752 of the workpiece on the piston, as well as between such features. The surface features 1752 may be disposed atop a layer 1740 of previously solidified powder or atop other material that is itself in contact with the piston. As shown in FIG. 7*b*, The user may then, by application of energy 1732 to particular regions of the powder layer, solidify the powder atop the structures (thus lengthening the structures), without also solidifying powder disposed between the structures. The results of this approach are shown in FIG. 7*c*, which illustrates the upper face 1402 of the piston 1410, having structures 1752 with curable powder 1760 on top of them and excess powder 1750 disposed between the structures. The powder is then solidified by application of energy 1732 from a source 1730. By repeating these steps, the user can create and grow structures 1752 that extend from the surface of the workpiece. As in the other embodiments, excess powder 1750 is suitably removed, as shown by the difference between FIGS. 7*d* and 7*e*, which figures illustrate that powder 1750 is removed from the structures 1752 and the upper face 1402 of the piston 1410.

Structures may also be constructed where at least a portion of the solidified material may be selectively removed at a later point in time. For example, a user might construct a cylindrical body having narrow strips of a sacrificial material that run across the diameter of the body. Once these sacrificial strips are removed (e.g., by etching) the user is left with a cylindrical body that has pores across its diameter, the pores corresponding to the former location of the sacrificial strips.

In some cases, a distortion or unwanted feature may develop in a part during construction. Without being bound to any particular theory, it is suspected that distortions may be a result of temperature gradients forming within the part during fabrication. To address these distortions, the process chamber may be heated so as to reduce the temperature gradient between the bulk of a part and the portion of the part being welded or sintered.

The user may, in some instances, elect to form a part that includes a sacrificial portion that is removed when the part is completed or before the part is used. This may be done such that distortions that are caused by mechanical interactions between the piston or platform face and the portion of the part that contacts the face are contained in a sacrificial portion of the part. For example, the user may desire to construct an implant body that is 10 cm in length. The user may then construct a body that is 12 cm in length and remove the 2 cm of the body that were closest to the piston or platform face during manufacturing.

In this way, the user may design a part in which the section of the part that is likely to contain defects (or that does contain defects) is removed. Bodies may be of virtually any size. As one example, screws having a diameter of about 0.5 mm or even 1 mm and a length of about 4 mm may be constructed. Bone plates having lengths of centimeters or even tens of centimeters may be constructed. Such bone plates may have a cross-section of 5 mm×50 mm, or 10 mm×30 mm, or other suitable cross section.

While not shown, manufacture may be performed in a process chamber. The process chamber may be at a essentially an ambient pressure, although pressures above and below ambient pressure are suitable, including near vacuum. The chamber may be filled with an inert gas (including noble gases). Nitrogen is considered a suitable working gas when the methods are being used to process steel, steel alloys, aluminum, copper alloys, silver, and the like. Argon is considered suitable when working with titanium alloys. In some embodiments, fumes are produced from the solidification of the powder. Such fumes are suitably removed; in some cases, fumes can interfere with the operation of an energy beam that is directed toward the powder. Fumes are suitably removed by circulating the contents of the chamber (including any gases) through the chamber and through a filter.

The methods may also be used to form implants or bodies in response to a user's specific needs or requirements. For example, a user may input into a system the dimensions and mechanical properties of a desired implant. The system may then fabricate an implant in response to the user's requirements. A user may, based on a fracture of a particular bone, require an implant of certain dimensions, with a flexible region at a particular position. In response to the user's requirements, the claimed systems can be used to produce a suitable implant. The system may be connected remotely to a physician, who can input fabrication instructions remotely to the system for body fabrication. In this way, one may construct customized bodies for individual patient use. One may effectively construct such bodies on-demand, in response to specific requests from clinicians.

The rigidity and flexibility of the different portions of the implant will depend, of course, on the user's needs. In some embodiments, a rigid region may have a modulus of elasticity of between about 90 and 250 GPa. Titanium and its alloys may have a modulus of elasticity of approx 110 GPa; steel and cobalt chromium alloys may have an elastic modulus of about 200 GPa. The flexible region may have a modulus of elasticity of between about 2.5 and 9 GPa; PEEK has a modulus of elasticity of about 3.5 GPa. The ratio of modulus (or other property) between the rigid and flexible regions may be set depending on the needs of the user. For example the flexible region may be only fractionally more flexible than the rigid region. In other embodiments, the flexible region may be substantially more flexible than the rigid region. In some embodiments (not shown), the difference in modulus (or other mechanical property) between the flexible and rigid regions may be 1%, 5%, 15%, 50%, 75%, 100%, 300%, or more.

While the attached figures illustrate the use of the disclosed bodies to stabilize a fractured bone, the bodies are not limited to fracture treatment. In one embodiment, the bodies may be used to support a bone that suffers from (or is predicted to suffer from) osteoporosis or other similar condition. The bodies may also be used as implants to replace part or all of a damaged or removed bone.

The disclosed bodies may also be provided as part of a system. Such a system may include a kit or other package that includes a variety of implants of different configurations, and a clinician may select from that package that implant that is most suitable.

A variety of implants, bodies, and parts are disclosed herein; the terms "implant," "body," and "part," are used synonymously. The disclosed methods and systems may be used to manufacture these and other parts.

In one embodiment, parts may comprise implants configured to be attached to an underlying bone so as to provide stability to the underlying bone. By reference to exemplary, non-limiting FIG. 1, such implants suitably include a first region 12*a* configured to be attached to an underlying bone 16; and a second region 12*b* disposed adjacent the first region 12*a*, the second region having a flexibility greater than that of the first region, and the second region being integral with the first region. Further reference will now be made to the figures to describe the disclosed bodies.

Figure 8:
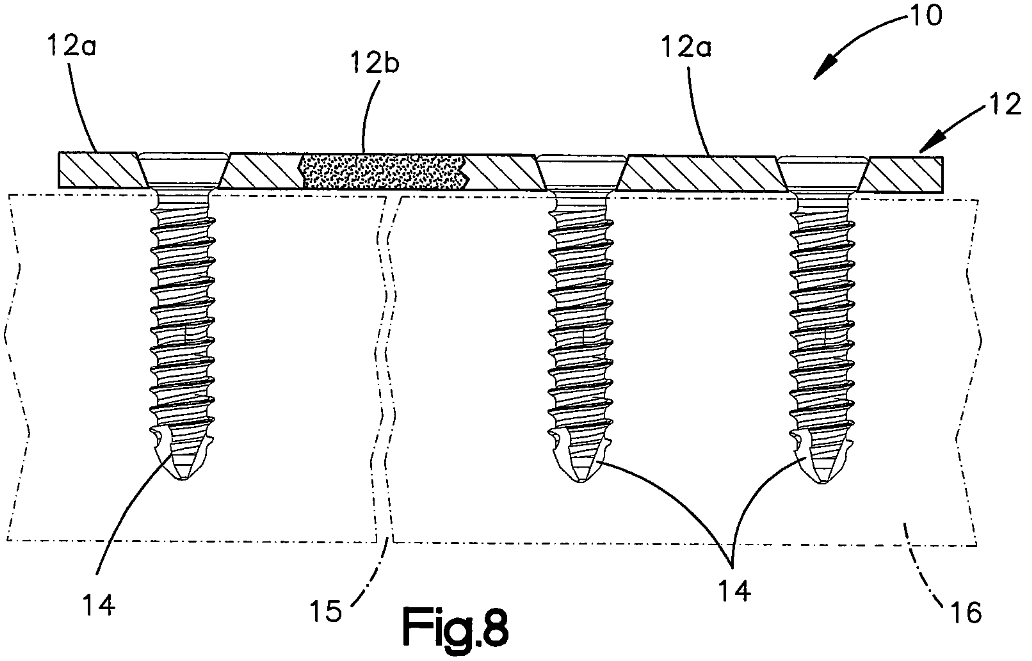
FIG. 8 illustrates a cross-sectional view of a bone plate having an integrated multi-material construction in accordance with a first preferred embodiment of the present application, the plate being mounted to a bone.

Referring first to FIG. 8, a bone joining integrated multi-material medical implant in accordance with a first preferred embodiment is comprised of a bone plate 12 with bone fixation screws 14 to mount the plate 12 to a bone 16, preferably across a fracture 15. The bone plate 12 preferably includes a rigid portion (first region) 12*a* constructed of a single generally rigid material where the bone fixation screws 14 secure the plate 12 to the bone 16 and a composite or flexible portion 12*b* that spans the fracture 15.

The rigid portion 12*a* is preferably anatomically shaped or otherwise configured to conform to the subject. The rigid portion also suitably includes bone contact areas to engage the bone 16, and the rigid portion is also suitably relatively stiff and strong in order to securely engage the bone screws 14.

The rigid portion 12*a* is preferably comprised of a stiff, strong metallic material, such as titanium, stainless steel or other biocompatible material that is able to take on the general size and shape of the rigid portion 12*a* and withstand the normal operating condition of the rigid portion 12*a*. Suitable plastics, metals, and even plastic-metal blends or alloys may also be used in the rigid region.

The composite or flexible portion 12*b* (second region) is preferably integrally formed with the rigid portion 12*a*. This second region may include one or even multiple materials that together adapt the material properties of the composite or flexible portion 12*b* as desired by the designer. Specifically, the composite or flexible portion 12*b* is adaptable to have a range of stiffness that is adapted for the specific biomechanical features of the bone 16 that is being repaired, the type of fracture 15 encountered or other anatomical or biomechanical features desired by the user. Accordingly, the composite or flexible portion 12*b* may have a relatively high stiffness to maintain major fragments of the bone in a permanent position or alignment following fixation. Such adaptation of the bone plate 12 may be appropriate for reconstructive surgery.

The composite or flexible portion 12*b* may have a reduced stiffness to repair a fracture and drive additional load through the bone 16 and fracture 15, as opposed to driving the load through the bone plate 12, to stimulate bone growth or in spinal fixation surgery to direct load to the vertebrae that are being fused, thereby promoting bone growth and limiting stress shielding. In this way, the user may configure a body so as to optimally direct body forces to or away from a fracture so as to promote optimal healing.

The bone plate 12 may be treated with etching, anodization, anodic plasma chemical processes or other coatings, such as electrolytic deposition or plasma spraying to enhance osseo-integration and bone growth on or into the bone plate 12. The surfaces may also be roughened mechanically or during the manufacturing process, as will be described in greater detail below, to facilitate attachment of bone substitute material, antibiotic agent deposition or other coatings or materials that are desirable for user.

The construction of the composite or flexible portion 12*b* with multiple materials permits the designer to adapt the stiffness and/or strength of the composite or flexible portion 12*b* to closely imitate the anatomical or biomechanical properties of the bone being treated or to effect a the load sharing the designer desires to create between the bone plate 12 and the bone.

The preferred bone plate 12 may be manufactured in a one step production process to form the two materials together in the composite or flexible portion 12*b*, as will be described in greater detail below. In addition, the manufacturing process incorporates one-material or homogenous portions, such as the rigid portion 12*a*, integrally with the composite or flexible portion 12*b*, as will also be described in greater detail below.

The body 10 may be a bar, a plate, or virtually any other conformation. The body may have a constant cross-section or a varying cross-section. The body may contain a single flexible region or multiple flexible regions. The flexible region may include one flexible material. The flexible region may include two or more flexible materials; it may be composed of a blend or materials or even of separate (e.g., alternating) regions of material. The rigid region may, similarly, include a single material, multiple materials, or even multiple regions of different materials. The anchors 14 may be screws, nails, and the like. Suitable anchors will be selected depending on the user's needs, and will be known to those of skill in the art.

The transition between flexible material 12*b* and the more rigid material 12*a* is shown here as being a discrete transition. This need not always be the case, as the disclosed monolithic bodies (also referred to as parts, in some instances) may also include regions that have a more gradual transition between two materials, or two regions. As described elsewhere herein, e.g., FIG. 4, these transitions may be effected by constructing a part layer-by-layer, where successive (adjacent) layers contain slightly different proportions of materials. For example, a first layer may include 100% metal. The next adjacent layer may be 99% metal, and 1% plastic. The next layer may be 98% metal and 2% plastic, and so on, so as to effect a gradual transition. Depending on the desired properties and on the characteristics of the materials (metal, polymer, and the like) being used, such a gradual transition may be used, which results in a material gradient between two or more regions of the body. Materials with similar melting temperatures may be matched together to form such a gradual transition between materials or regions.

Figure 16A:
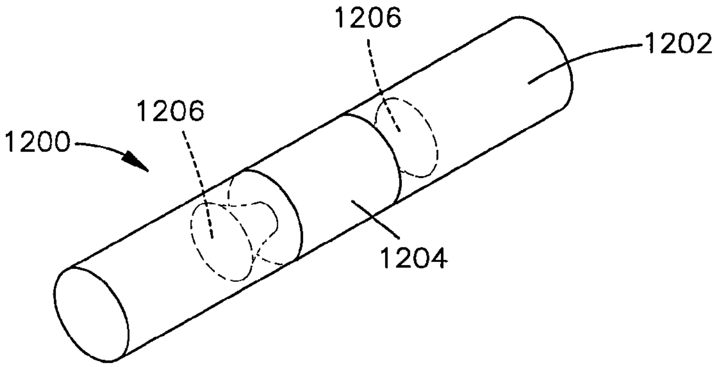
FIG. 16A illustrates an implant comprising multiple material regions.

The first and second regions are suitably integral with one another. Integral may relate to embodiments where the first a second regions are structurally interlocked with one another. This is shown in FIG. 16A. In that embodiment, the body

1200 includes a first, rigid region 1202 and a second, more flexible region 1204. The second region 1204 is formed such that projections 1206 are effectively encased by the first region 1202, such that the first and second regions are mechanically interlocked with one another. This mechanical interlocking is accomplished without adhesive or mechanical anchors (e.g., nails, screws, and the like), although such reinforcements may be used.

Figure 16B:
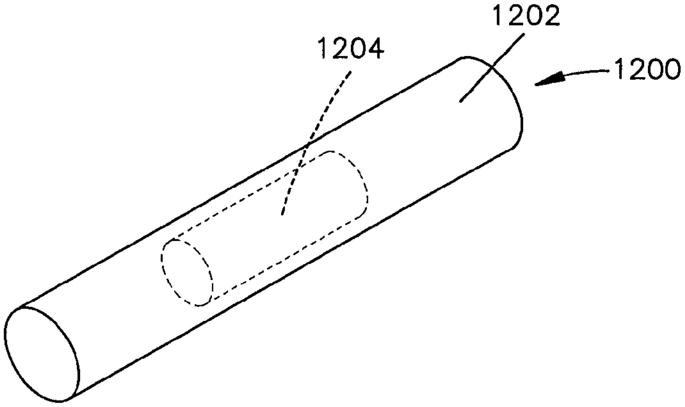
FIG. 16B illustrates an implant comprising multiple material regions.
Figure 17:
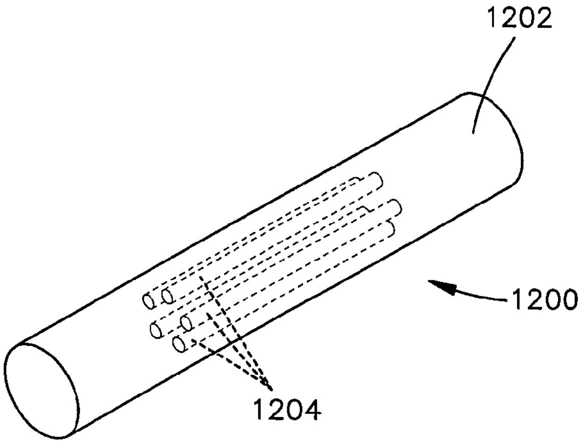
FIG. 17 illustrates an implant comprising multiple material regions.

FIG. 16B illustrates an alternative body 1200 wherein the second (flexible) region 1204 is entirely encased within the first (rigid) region 1201. Alternatively (not shown), the rigid (first) region may be encased within the flexible (second) region. FIG. 17 illustrates yet another embodiment, wherein the body 1200 includes multiple second (flexible) regions 1204 that are disposed within the first (rigid) region 1202.

In some embodiments, the first and second regions are attached to one another by way of a transition region between the two regions, the transition region comprising a mixture of a material of the first region and a material of the second region. For example, a body might include a transition zone between the first and second regions, where the zone transitions from 100% first material, to a ration of 99:1 of first material to second material, to a ration of 98:2 first material to second material, and so on. In this way, the user may fabricate a body that includes a gradual transition from one material to another.

When powder is solidified in some embodiments, it may be made molten at specific locations to be joined to the underlying material, which underlying material may be a previously-solidified layer of powder. This may be effected by, inter alia, a laser beam, (e.g. Diode pulsed fiber laser), an electron beam, and the like.

Figure 9:
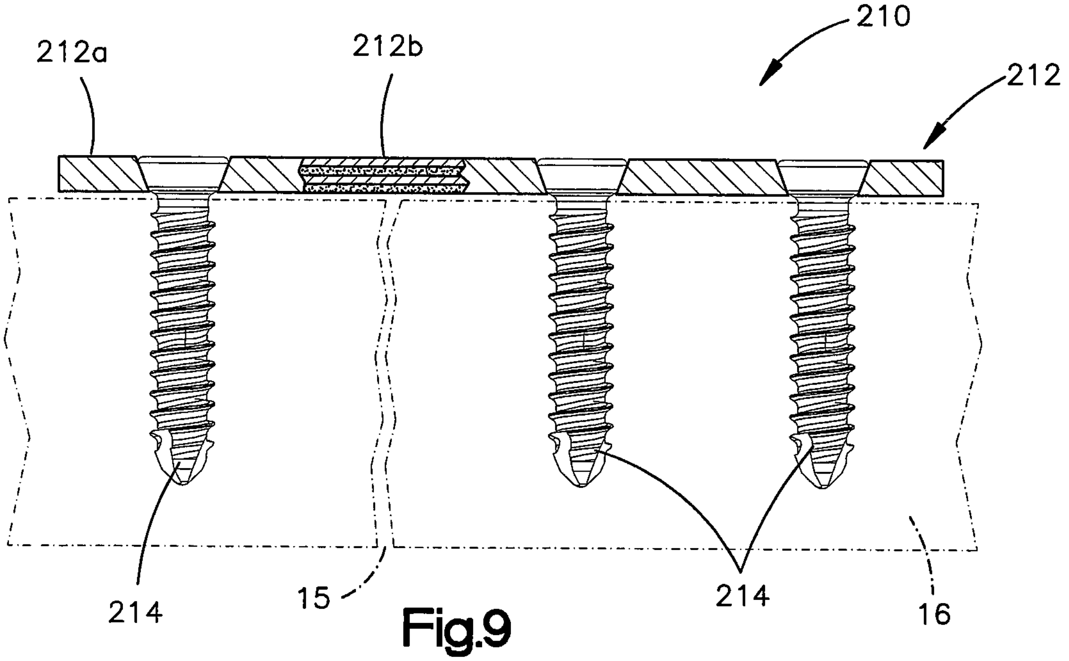
FIG. 9 illustrates a cross-sectional view of a bone plate having an integrated multi-material construction in accordance with a second preferred embodiment of the present application, the plate being mounted to a bone.

Referring to FIGS. 8 and 9, in the second preferred embodiment an integrated multi-material medical implants 10 and 210 are constructed in a similar manner to the integrated multi-material implant 10 in accordance with the first preferred embodiment. Like reference numerals are utilized to identify like components when comparing the second preferred embodiment to the first preferred embodiment with a prefix "2" utilized to specifically identify components of the second preferred embodiment.

Referring now to FIGS. 8-15, in the second preferred embodiment the composite or flexible portion 212*b* is arranged in a different manner than the composite or flexible portion 12*b* of the first preferred embodiment in FIG. 8. Specifically, in the second preferred embodiment, the composite or flexible portion 212*b* is constructed of distinct layers of a first material 222 and a second material 224 (with reference to FIG. 6). Thus, the second (more flexible) region may thus include two or materials. A region may—as shown in FIG. 9—also include two or more sub-regions, which sub-regions may each comprises a different material. For example, a body might have a rigid region 212*a* and a flexible region 212*b*, wherein the flexible region includes alternating strips of two or more different materials, as shown by 212*b*. Sub-regions within a region may be arranged in virtually any pattern that suits the needs of the user.

Likewise, the first (rigid) region may also be of varying configurations. The first region may include one, two, or more materials. The first region may also include one or more sub-regions. For example, a first region might comprise stainless steel, but may include an aperture formed in a titanium section of the first region. The first region may also be configured such that it includes strips of different materials.

The first (rigid) region may also include sub-regions that are disposed adjacent to the second (flexible) region. For example, FIG. 8 shows a body 10 wherein the second region

12*b* is flanked on both sides by rigid regions 12*a*. A body may have two or more flexible regions; such bodies are useful in the treatment of bones having multiple fractures. A body might have three or more flexible sub-regions. Similarly, a body may include one, two, three, or even more rigid sub-regions.

The first region, the second region, or both, may comprise a biocompatible material, although biocompatibility is not a requirement. As described elsewhere herein, the first region is suitably adapted for fixation to a bone. The body may thus include an aperture (not labeled) or hole disposed in the rigid region, through which aperture or hole a fixation member (nail, anchor, screw, and the like) may be installed so as to affix the body to the bone. One non-limiting embodiment is shown in FIG. 1, which shows a fixation screw 14 installed through an aperture formed in a rigid region of the multimaterial implant. Such an aperture may include internal threads so as to engage with complementary threads of an anchor. The SynFix™ system from Synthes (www.synthes.com) is one such suitable anchor system.

While the body 10 in FIG. 8 does not include such features, the bodies may also define one or more voids, gaps, spaces, pores, grooves, or even a mesh. Such voids may be enclosed within the body. Alternatively, such voids may be disposed on the exterior of the body, such as along a surface of the body. The voids may provide a location for bone in-growth. The voids may be filled or coated with a chemical reactant, such as an antibiotic, a growth factor, an analgesic, and the like.

The bodies may also include additional materials. For example, a body may include particles (e.g., silver nanoparticles) that are dispensed into or onto the body. A robotic arm, a sprayer, and the like are all suitable ways to introduce additional materials into or onto the bodies. A portion (or even all) of an implant's exterior surface may be coated; such materials may include drugs, growth factors, and the like. An implant may be coated in a biocompatible material (e.g., polyethylene). In this manner, an implant may be formed from materials that are not perfectly biocompatible, but may then be coated or laminated with a biocompatible material.

Also not shown in FIG. 8, the bodies or implants may include features that are adapted to engage a bone. Such features may be ridges, teeth, spikes, hooks, knurls, splines, and the like.

The entire rigid portion 212*a* is preferably constructed from the first material 222 and the flexible portion 212*b* preferably includes layers of the first material 222. In the second preferred embodiment, the first material 222 is preferably comprised of a relatively stiff, strong, biocompatible metal material such as titanium, stainless steel, aluminum or alternative appropriate materials. The second material 224 is preferably constructed of a lower stiffness material such as polyether ether ketone ("PEEK") or other polymeric material that has a lower stiffness than the first material 222 such that the composite or flexible portion 12*b* may be constructed and adapted by the user to have a range of stiffnesses depending upon the material make-up and arrangement of the first and second materials 222, 224 in the composite or flexible portion 12*b*.

In contrast, in the first preferred embodiment, the composite or flexible portion 12*b* is constructed of first and second materials that are not necessarily layered as described in the second preferred embodiment but are nonetheless adaptable to tailor the properties of the composite or flexible portion 12*b*.

The bone plates 12, 212 of the first and second preferred embodiments are preferably utilized to promote biologic repair of the fracture 15 in the bone 16. The preferred bone plates 12, 212 permit some flexibility to bridge the fracture 15 and promote callus formation, which may stabilize the fracture 15 in a more biologically correct manner than a typical rigid bone plate, as would be apparent to one having ordinary skill in the art. The preferred bone plates 12, 212 with the composite or flexible portions 12*b*, 212*b*, generally permit additional load transfer to the bone and the fracture such that the remodeled bone at the fracture 15 is carrying a major part of any load encountered by the bone 16 during healing.

Figure 10:
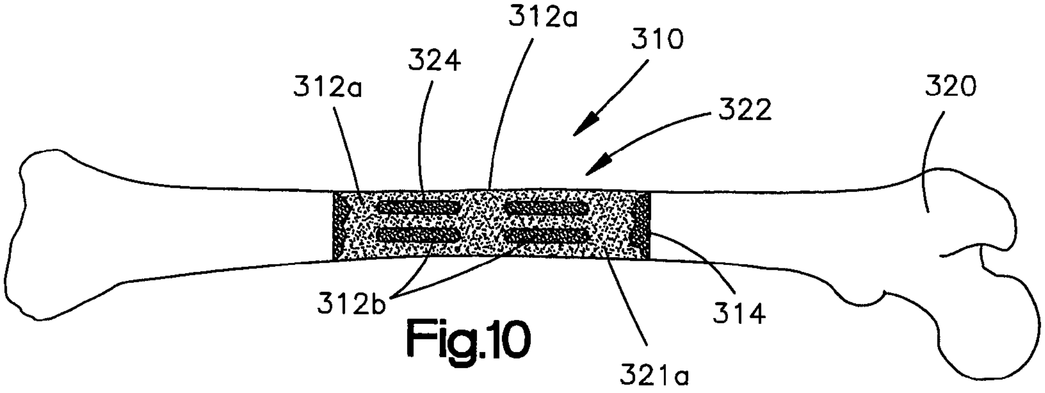
FIG. 10 illustrates a side elevation view of a bone joining implant in accordance with a third preferred embodiment of the present application, the bone joining implant being mounted to a bone.
Figure 11:
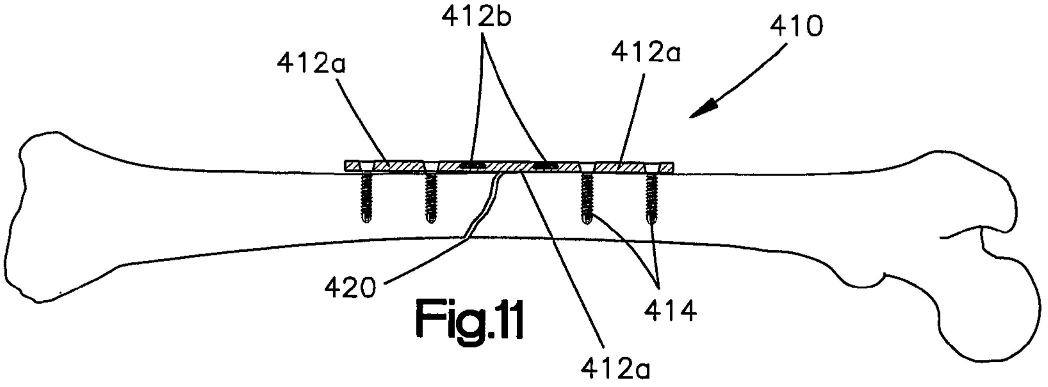
FIG. 11 illustrates a side elevation view of a bone plate in accordance with a fourth preferred embodiment of the present application, the plate being mounted to a bone.

Referring to FIGS. 9-11, integrated multi-material medical bone joining implants 310, 410, 510 in accordance with third, fourth and fifth preferred embodiments of the present application are similar to the bone joining implants 10, 210 of the first and second preferred embodiments. Like reference numerals are utilized to indicate like or similar elements of the bone joining implants 310, 410, 510 of the third, fourth and fifth preferred embodiment with a prefix "3" to identify the third preferred embodiment, a prefix "4" to identify components of the fourth preferred embodiment and a prefix "5" to identify components of the fifth preferred embodiment.

In the third preferred embodiment, the bone plate or bone joining implant 312 preferably bridges a fracture between two bony structures. The fracture may be at a portion of a long bone 320 or may be placed into an intervertebral space between vertebrae during spine surgery (not shown). The bone joining component 312 of the third preferred embodiment includes two composite or flexible components 312*b* with first and second materials 322, 324 included in a single slice of the bone joining component 312 taken generally parallel to a longitudinal axis. The bone joining component 312 of the third preferred embodiment is not limited to including two separate composite or flexible portions 312*b* and may include a single composite or flexible component or additional composite or flexible components depending upon the preferred design of the developer, the specific bone being manipulated or other factors that permit tailoring the bone joining implant 310 to a particular anatomic structure or bone.

The bone joining implant 310 of the third preferred embodiment also includes spikes or surface roughening 314 at opposing ends to secure the bone joining implant 310 to the bone. The bone joining implant 310 of the third preferred embodiment is not limited to including the spikes or surface roughening 314 to secure the bone joining component 312 to the bone and may include screws, plants, adhesive bonding devices or other mechanisms to secure the bone joining component 312 to the bone. In addition, the fracture may be secondarily supported by a plate and screws, such as the above-described bone joining implants 10, 210 of the first and second preferred embodiments.

The implant 310 may be inserted so as to connect two regions of a fractured bone 320 (not shown). In this embodiment, the ends of the implant may be glued or otherwise affixed to the faces of the fracture. The ends of the implant may also be mechanically affixed (e.g., via anchors or bone screws) inserted to as to maintain the body in position.

Referring to FIG. 11, in the fourth preferred embodiment, the bone joining implant 410 is comprised of a bone plate 412 that spans the fracture 420 in a similar manner to the bone plates 12, 212 of the first and second preferred embodiments. However, the preferred bone plate 412 of the fourth preferred embodiment includes two composite or flexible proportions 412*b* that span the fracture 420. Such a construction may permit the designer to further tailor portions of the bone plate 412 to the anatomical or biomechanical features of the bone B that is being treated. In addition, similar constructions may be employed to provide screw holes in three or more rigid portions 412*a*, each separated by at least one of the flexible portions 412*b* such that the flexible portions 412*b* span several fractures 420 in the bone.

Figure 12:
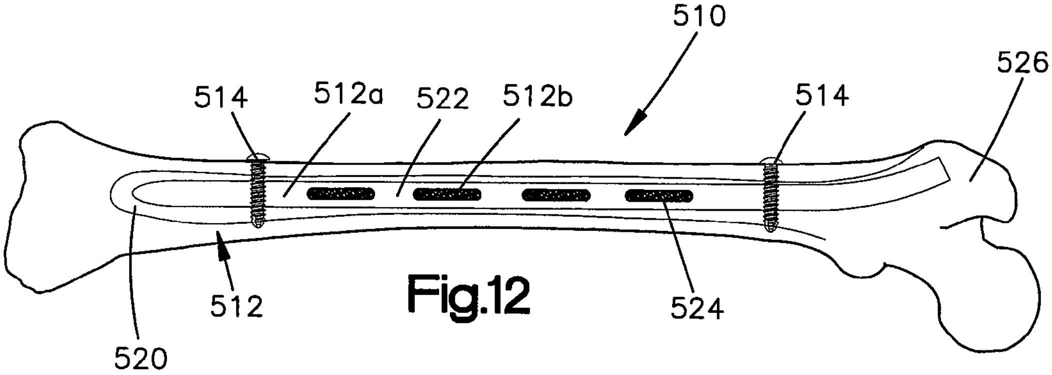
FIG. 12 illustrates a side elevation view of an intramedullary nail in accordance with a fifth preferred embodiment of the present application, the intramedullary nail being mounted to a bone.

Referring to FIG. 12, in a fifth preferred embodiment, the bone joining component 512 is in the form of an intramedullary nail that is preferably positioned within an intramedullary canal 520 of the bone 526 in an implanted configuration. The preferred bone joining component 512 of the fifth preferred embodiment includes multiple composite or flexible portions 512*b* and multiple rigid portions 512*a* to adapt the nail 512 and its mechanical features as desired by designer. The nail 512 is preferably secured to the bone 520 by bone fixation screws 14 that engage the bone 526 on both sides of the intramedullary canal 520.

Referring to the figures, the composite or flexible portions 12*b*, 212*b*, 312*b*, 412*b*, 512*b* of the bone joining component or bone plates 12, 212, 312, 412, 512 preferably have the above-described composite structures with limited open pores that may reduce fatigue strength, second materials 224, 324, 424, 524 that are comprised of polymeric materials that generally avoid plastic deformation of the first, metallic material 222, 322, 422, 522, generally smooth, continuous first metal materials 222, 322, 422, 522 that maintain notch strength and the second, polymeric materials 224, 324, 424, 524 are limited from becoming plastically deformed due to the surrounding first, metallic material 222, 322, 422, 522.

Figure 14:
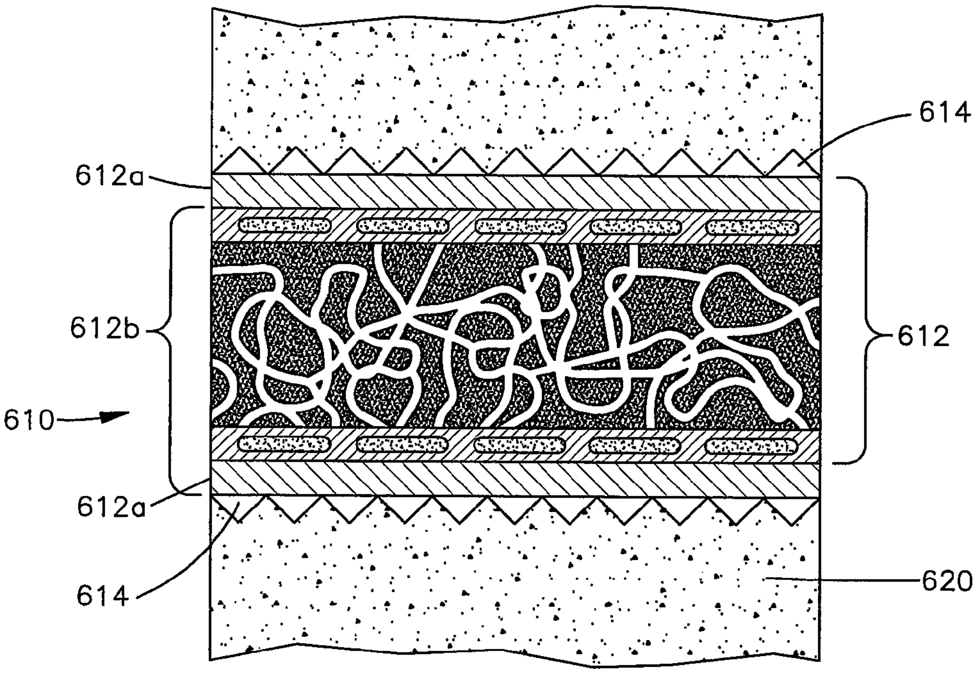
FIG. 14 illustrates a cross-sectional view of a bone joining implant in accordance with a sixth preferred embodiment of the present application, the bone joining implant being mounted between two bone fragments.

Referring to FIG. 14, an integrated multi-material medical bone joining implant 710 is similar to the above-described bone joining implants 10, 210, 310, 410, 510 and like reference numerals are utilized to identify like elements with a prefix "6" utilized to identify specific components of the sixth preferred embodiment.

The bone joining component 612 of the sixth preferred embodiment includes spikes 614 on opposing ends that are utilized to primarily or initially secure the bone joining implant 610 to the bone 620. The bone joining implant 610 of the sixth preferred embodiment includes relatively narrow rigid portions 612*a* proximate the spikes 614 and a variety of structures and combinations of materials that make up the composite or flexible portion 612*b*. The bone joining implant 610 of the sixth preferred embodiment exemplifies the adaptability of the manufacturing process to provide multiple structures, shapes and materials in the composite or flexible portion 612*b* to adapt the bone joining implant 612 to the biological, anatomical or general needs of the fracture or bone being treated.

For example, different varieties of materials and combinations may be used throughout the composite or flexible portion 12*b* to smooth the transition between the rigid portion 12*a* and a highly elastic central portion of the composite or flexible portion 612*b* or to facilitate other desired properties in the composite or flexible portion 612*b*. Such areas in the composite or flexible portion 612*b* that transition between the rigid portion 12*a* and a highly elastic central portion may harmonize stress shielding between the rigid portion 612*a* and the soft core of the composite or flexible portion 612*b*.

Figure 15B:
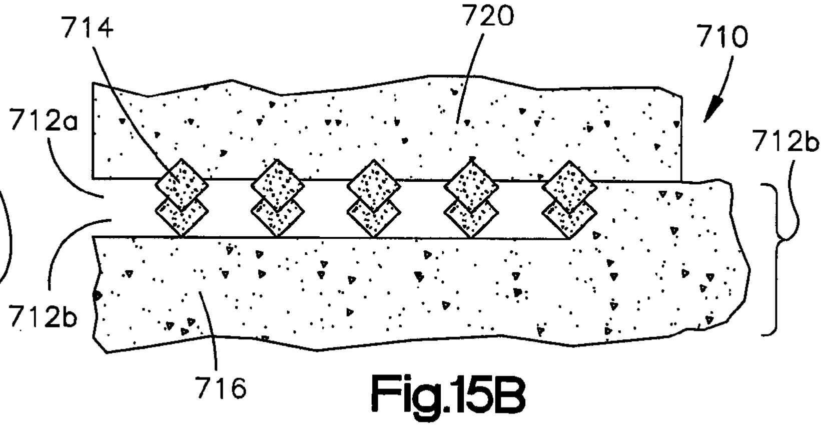
FIG. 15B illustrates a cross-sectional view of the bone joining nucleus replacement device of FIG. 15A taken along a sagittal plan.

Referring to FIGS. 15A and 15B, a bone joining implant 710 in accordance with a seventh preferred embodiment is similar to the above-described preferred embodiments and like features are identified by like reference numerals with a prefix, "7" utilized to identify the specific features of the seventh preferred embodiment.

The bone joining implant 710 of the seventh preferred embodiment is constructed and adapted as a nucleus replacement device. The nucleus replacement bone joining implant 710 of the seventh preferred embodiment may include spikes 714 to secure the bone joining component 712 to a vertebra 720 and a relatively elastic or soft core 716 that preferably mimics the properties of a nucleus 730 of an intervertebral disc. The soft core 716 is constructed of a hydroelastic material, potentially a hydrogel or other material that has mechanical properties similar to those of the nucleus 730 of an intervertebral disc.

The preferred manufacturing process, which will be described in greater detail below, permits forming of the spikes 714 from a relatively stiff, strong material such as titanium and a transition zone between the rigid portion 712*a* and the soft core 716 by incorporating the multiple materials of the composite or flexible portion 712*b*. The bone joining component 712 of the seventh preferred embodiment may be constructed of several biocompatible component materials that are bone friendly, such as titanium, titanium alloys, hydroxyapatite or other biocompatible materials that are generally known to those having ordinary skill in the art.

A body may be configured so as to be more flexible—or more rigid—in a particular direction. For example, a body may be configured so as to be comparatively easy to bend in one direction, but not in the opposing direction. This may be effected by the placement and construction of flexible regions within the body so as to give rise to the particular mechanical properties of the body. For example, although the body 1202 of FIG. 12B includes a flexible region 1204 at the center of the body, the flexible region may be disposed closer to one edge or surface of the body so as to impart a particular flexibility in one direction. A flexible (second) region of a body may be formed in a triangle or even a pyramid so as to promote flexibility in only specified directions.

FIG. 12A illustrates non-limiting embodiments of the claimed bodies. As shown, a body 1200 may include a flexible region 1204 that is disposed between two more rigid regions 1202. The body may be constructed such that—as shown—the flexible region is effectively anchored into one or more rigid regions. In the non-limiting embodiment of FIG. 12, the flexible portion is cast such that trumpet-shaped portions 1206 of the flexible region extend and are anchored into the rigid regions flanking the flexible region. While the extensions of the flexible region in FIG. 12 are trumpet-shaped, a variety of configurations may be used so as to anchor flexible and rigid regions together. As shown in FIG. 12, a portion of the flexible region may be exposed to the environment exterior to the body.

FIG. 12B also illustrates an alternative embodiment wherein a flexible region 1204 is contained entirely within the implant body 1200. In this figure, a cylindrical region of flexible material is contained within the larger body, which larger body is made from a rigid material 1202, such as a metal. This configuration confers some flexibility on the body itself at the location of the flexible region. For example, the body shown in FIG. 12B could be anchored at either end with anchors (not shown), with the flexible region positioned over a bone fracture.

The bodies may be constructed such that the rigid material has some flexibility (i.e., is not perfectly rigid) and is comparatively more rigid than the flexible material used in the body. In this way, the region of the body shown in FIG. 12B having a flexible region fully contained within the body is itself flexible.

Figure 13:
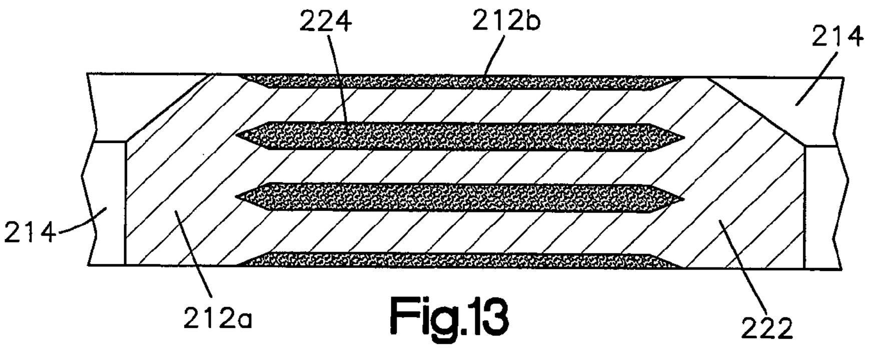
FIG. 13 illustrates a greatly magnified side elevation view of the plate of FIG. 8.

FIG. 13 is a further, exemplary embodiment of the claimed bodies. As shown in that figure, a body 1200 may contain multiple flexible regions 1204 within a more rigid region 1202. A body may also (not shown) contain multiple rigid regions within a flexible region. Such embodiments may be useful where the user desires a body that is to fit snugly within a particular space (particularly a space that is irregular in shape) but that also provides rigidity.

The systems also suitably include a powder removal device configured to remove powder from the vertically-moveable platform. As described elsewhere herein, the user may expose a solidified portion of powder by advancing the platform upward so that excess or unsolidified powder may be removed. This removal may be effected by brushing, vacuuming, blowing, precipitating (e.g., via static electricity or electrostatics), application of a magnetic force, or by other methods known in the art.

Powder may be transferred from a powder container to the platform in a variety of ways. In one embodiment, the powder is dispensed directly onto the platform from a powder container disposed above the platform; in other embodiments, powder is disposed onto a layer (e.g., an already-solidified layer) that is supported by the platform. The powder may then be leveled so as to achieve a powder layer of the desired thickness (e.g., the thickness of a particle). Leveling may be effected by using a brush or scraper in the manner of a windshield wiper or crumb scraper to level the powder. The user may also apply vibrations or shaking (e.g., by ultrasound) to the powder so as to settle the powder and to form and level a powder layer. Vibrations (e.g., ultrasound) may also be used to remove excess or unwanted powder following a powder solidification step.

As shown in FIGS. 1A and 1B, powder may also be transferred—e.g., by sweeping, brushing, and the like—to the platform from a powder-dispensing piston. This transfer may be effected by a steel or synthetic blade that pushes the powder over area to be processed. A steel blade may be used, as such blades facilitate increased material density for comparatively large pieces (i.e., more than 4 mm in cross section) or particles that have little to no fine elements that are less than about 4 mm in cross section. Synthetic wiper blades are considered suitable for addressing powders that have comparatively small cross sections (<4 mm) or have small features. Smaller particles may, in some embodiments, be processed using comparatively lower blade/sweeping velocities. A brush blade that has steel fibers of about 0.1 mm is considered particularly suitable, particularly where powder particles may have comparatively small cross-sections or other features of less than about 4 mm. A similar brush that uses synthetic fibers may also be suitable for use in the claimed methods. The brush material may be selected to as to reduce or avoid static charging during operation.

The systems also suitably include a chamber in which powder processing is performed. The chamber may be sealed against the external environment. The systems also suitably include a device or arrangement of devices for fume handling, for the introduction of gas to the chamber, or both. The fume handling system may be configured so as to remove or filter fumes or gases from the chamber. The system may also be configured to introduce a working gas (such as an inert gas) to the chamber.

The systems may also include a temperature control system, a humidity control system, or both. The user may manipulate the environment within the chamber so as to achieve optimal processing. The system may also, in some embodiments, include a device to pick up or otherwise manipulate bodies that are formed by the disclosed methods. Such devices may be used to pick completed parts up and prepare the parts for packaging or for use. In some embodiments, the device may be used to pick a workpiece up and invert or otherwise reorient the workpiece for further processing. The system may include a device for dispensing liquids into or onto a workpiece; as described elsewhere herein, bodies may be formed that include voids into which a fluid may be dispensed. The dispenser may also be used to dispense a preservative or other fluid (or even gas) into packaging into which a finished body is placed.

The optimal orientation of the material being processed relative to the movement of any powder spreaders will depend on the user's needs. In pieces that have a downward inclination or angle, it may be advantageous (though not necessary) to have the powder spreader spread powder toward the inclination from behind the inclination. Powder may also be spread parallel to an edge or inclination of a body being constructed, or even at an angle to the edge. In some embodiments, successive layers may be applied by powder spreaders that spread powder in opposite directions from one another. In other embodiments, successive layers may be applied by spreaders that are oriented at 90 degrees (or 270 degrees) from one another. A spreader may be oriented so as to spread powder along a minor or major axis of a body being formed; the spreader may also be configured to spread powder in a direction that is angled relative to an axis of the body.

It will be appreciated by those skilled in the art that changes could be made to the embodiments described above without departing from the broad disclosed concept thereof. It is understood, therefore, that this invention is not limited to the particular embodiments disclosed, but it is intended to cover modifications within the spirit and scope of the present invention as defined by the present description.

What is claimed:

1. An implant for stabilizing a fracture in an underlying bone, the implant comprising:

a first region comprising a first material configured to be attached to the underlying bone; and a second region comprising a second material that is different than the first material, the second region being disposed adjacent the first region, the second region having a flexibility different than that of the first region, the first and second regions being monolithic with one another, the first region comprising at least one aperture configured to receive an anchor configured to secure the implant to the underlying bone, and the implant being configured for installation across a fracture in the underlying bone so as to provide stability to the underlying bone.

2. The implant of claim 1, wherein the first and second regions are structurally interlocked with one another.

3. The implant of claim 1, wherein the first and second regions are attached to one another by way of a transition region between the two regions, the transition region comprising a mixture of a material of the first region and a material of the second region.

4. The implant of claim 1, wherein at least one of the first region and the second region comprises a biocompatible material.

5. The implant of claim 1, wherein the first region comprises two or more materials.

6. The implant of claim 1, wherein the first region comprises two or more sub-regions.

7. The implant of claim 1, wherein the second region comprises two or more materials.

8. The implant of claim 1, wherein the second region comprises two or more sub-regions.

9. The implant of claim 1, wherein a surface of the implant defines one or more voids.

10. The implant of claim 1, wherein a surface of the implant comprises spikes adapted to secure into a bone.

11. The implant of claim 1, wherein the first region comprises two sub-regions disposed adjacent to the second region.

12. The implant of claim 1, wherein the second region is characterized as being encased within the first region.

13. The implant of claim 1, wherein the first region is characterized as being encased within the second region.

14. The implant of claim 1, wherein the first region and the second region comprise at least two different materials.

15. The implant of claim 14, wherein the first region at least partially comprises at least one of titanium, stainless steel, or aluminum, and the second region at least partially comprises at least one of a plastic and PEEK.

16. The implant of claim 1, wherein each of the first and second regions define a plurality of discrete layers.

17. The implant of claim 16, wherein each of the layers are individually laser-processed.

18. The implant of claim 16, wherein each of the layers are individually solidified powder layers.

19. The implant of claim 16, wherein the second region has a flexibility greater than that of the first region.

20. The implant of claim 1, wherein the implant is configured so as to extend along a surface of the bone in which the fracture is present.

21. The implant of claim 1, wherein the implant is configured such that the second region lies adjacent to the fracture when the implant is installed.

22. The implant of claim 1, wherein the first region comprises a metal and wherein the second region comprises a polymer.

23. The implant of claim 22, wherein the metal comprises steel, titanium, aluminum, or any combination thereof.

24. The implant of claim 22, wherein the polymer comprises PEEK, polyethylene, or any combination thereof.

25. An implant for stabilizing a fracture in an underlying bone, the implant comprising:

a first region comprising a metal and the first region configured to be attached to the underlying bone; and a second region disposed adjacent the first region, the second region comprising a polymer and having a flexibility different than that of the first region, the first and second regions being monolithic with one another, the implant comprising a transition region between the two regions, the transition region comprising a mixture of the metal of the first region and the polymer of the second region, the first region comprising at least one aperture configured to receive an anchor configured to secure the implant to the underlying bone, and the implant being configured for installation across a fracture in the underlying bone so as to provide stability to the underlying bone.

26. The implant of claim 25, wherein the implant is configured such that the second region lies adjacent to the fracture when installed.

27. The implant of claim 25, wherein the metal comprises steel, titanium, aluminum, or any combination thereof.

28. The implant of claim 25, wherein the polymer comprises PEEK, polyethylene, or any combination thereof.

29. The implant of claim 25, wherein the implant is configured so as to extend along a surface of the bone in which the fracture is present.

* * * * *